United States Patent [19]

Yano et al.

[11] Patent Number: 5,480,899
[45] Date of Patent: Jan. 2, 1996

[54] OXAZOLIDINE DERIVATIVES AND PHARMACEUTICALLY ACCEPTABLE SALTS THEREOF

[75] Inventors: Shingo Yano; Tomoyasu Ohno, both of Hannou; Kazuo Ogawa; Haruo Yamada, both of Iruma; Tetsuhiko Shirasaka, Kawagoe; Hiroyuki Kawamura, Ichikawa; Shinichi Watanabe, Ohtsu, all of Japan

[73] Assignee: Taiho Pharmaceutical Co., Ltd., Tokyo, Japan

[21] Appl. No.: 167,798

[22] PCT Filed: Apr. 28, 1993

[86] PCT No.: PCT/JP93/00559

§ 371 Date: Dec. 21, 1993

§ 102(e) Date: Dec. 21, 1993

[87] PCT Pub. No.: WO93/22298

PCT Pub. Date: Nov. 11, 1993

[30] Foreign Application Priority Data

Apr. 30, 1992 [JP] Japan ................... 4-111773

[51] Int. Cl.$^6$ .................. C07D 263/24; A61K 31/42
[52] U.S. Cl. .................. 514/376; 514/340; 546/275; 548/229
[58] Field of Search .................. 514/376; 548/229

[56] References Cited

U.S. PATENT DOCUMENTS

| | | | |
|---|---|---|---|
| 3,020,262 | 2/1962 | Speranza | 548/229 |
| 4,602,093 | 7/1986 | Baldwin | 548/336 |
| 4,999,378 | 3/1991 | Fujii et al. | 514/567 |
| 5,145,865 | 9/1992 | Fujii et al. | 514/424 |

FOREIGN PATENT DOCUMENTS

| | | |
|---|---|---|
| 0086403 | 2/1983 | European Pat. Off. |
| 3-275666 | 12/1991 | Japan |
| 93-22298 | 11/1993 | WIPO |

OTHER PUBLICATIONS

Iwakura et al Chem. Abst. vol. 67, Entry 108577 (1966).
Ulrich et al. Jour. Org. Chem. vol. 34 No. 10 pp. 3200–3201 (1969).
Iwakura et al Yuki Gosei Kagaku Kyokaishi vol. 24, No. 1 pp. 60–65 (1966).
Breslow et al. Jour Am. Chem. Soc. vol. 72 pp. 4244–4246 (1950).
Iwakura et al. Chemical Abstracts, vol. 64, No. 6, 14 Mar. 1966, Entry 8163a.

*Primary Examiner*—Donald G. Daus
*Attorney, Agent, or Firm*—Nikaido, Marmelstein, Murray & Oram

[57] ABSTRACT

An oxazolidine derivative represented by the formula (I)

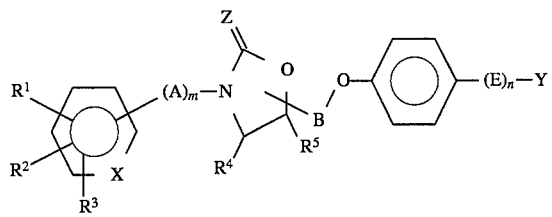

wherein $R^1$, $R^2$ and $R^3$ are H, optionally halogenated alkyl, optionally halogenated alkoxy, OH, halo, $NO_2$, amino optionally having acetyl or alkyl, COOH, alkoxycarbonyl, CN, alkanoyl, 2-oxazolyl, or $R^1$ and $R^2$ may be combined with each other to represent $-(CH_2)_p-$ or $-O(CH_2)_qO-$ (p is 3–5, q is 1–3) to form a ring, m and n are each 0 or 1, $R^4$ and $R^5$ are H or alkyl, X is C or N, Y is $CH_2OH$, CHO or $COOR^6$ ($R^6$ is alkyl, benzyl or H), A is alkylene, carbonyl or sulfonyl, B is alkylene, E is alkylene which may be substituted with halo or is alkenylene, Z is O or S, except for a compound wherein n is 0, m is 1 and Y is $CH_2OH$, and except for a compound wherein n is 0, Y is $COOR^6$ ($R^6$ is alkyl), a salt thereof, a process for its preparation, antihyperlipidemic composition containing the derivative as an active ingredient and a method for treating hyperlipidemia comprising administering the derivative.

11 Claims, No Drawings

OXAZOLIDINE DERIVATIVES AND PHARMACEUTICALLY ACCEPTABLE SALTS THEREOF

This is a 371 of PCT/JP93/00559 filed Apr. 28, 1993.

TECHNICAL FIELD

The present invention relates to novel oxazolidine derivatives and pharmaceutically acceptable salts thereof which have an activity to decrease triglyceride and cholesterol in the blood and which is useful as an anti-hyperlipidemic agent.

BACKGROUND ART

According to epidemiological investigation in Helsinki, it is considered that triglyceride and cholesterol in the blood are closely associated with the onset of hyperlipidemia (Circulation, 1992; vol. 85: 37–45). Therefore, for more effective and proper suppression of hyperlipidemia, it is desired to inhibit both the synthesis of triglyceride and cholesterol in the blood. Now there is a strong demand for the development of drugs capable of potently inhibiting their syntheses in the blood. However, while the phenylcarboxylic acid derivatives and the like disclosed in Japanese Unexamined Patent Publications Nos. 56452/1990 corresponding to U.S. Pat. No. 4,999,378, and 275666/1991 corresponding to U.S. Pat. No. 5,145,865 are known as compounds capable of lowering blood triglyceride and cholesterol, a compound which can satisfactorily produce the effect of lowering both of them has not yet been developed.

DISCLOSURE OF THE INVENTION

The present inventors conducted extensive research in view of the problems in the prior art and found that novel oxazolidine derivatives represented by the following formula (I) and pharmaceutically acceptable salts thereof have an excellent activity to inhibit the synthesis of triglyceride and activity to inhibit the synthesis of cholesterol and are useful as a medicament. The present invention has been accomplished based on this finding.

The present invention provides an oxazolidine derivative represented by the formula (I)

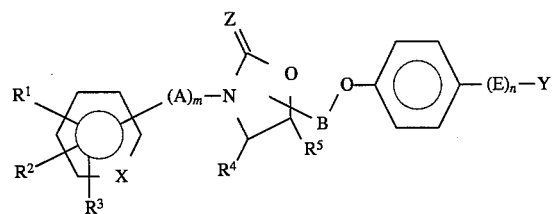

wherein $R^1$, $R^2$ and $R^3$ are the same or different, and each represents a hydrogen atom, a lower alkyl group optionally having one or more halogen atoms, a lower alkoxy group optionally having one or more halogen atoms, a hydroxyl group, a halogen atom, a nitro group, an amino group optionally having one or more acetyl or lower alkyl groups, a carboxyl group, a lower alkoxycarbonyl group, a cyano group, a lower alkanoyl group or a 2-oxazolyl group, or $R^1$ and $R^2$ may be combined with each other to represent an alkylene chain $-(CH_2)_p-$ or an alkylenedioxy chain $-O(CH_2)_qO-$ wherein p is 3, 4 or 5, q is 1, 2 or 3, thus forming a cyclic structure, m and n are each 0 or 1, $R^4$ and $R^5$ are the same or different and each represents a hydrogen atom or a lower alkyl group, X is a carbon atom or a nitrogen atom, Y is a hydroxymethyl group, an aldehyde group or a group represented by $COOR^6$ ($R^6$ is a lower alkyl group, a benzyl group or a hydrogen atom), A is a lower alkylene group, a carbonyl group or a sulfonyl group, B is a lower alkylene group, E is a lower alkylene group which may be substituted with a halogen atom or is a lower alkenylene group, Z is an oxygen atom or a sulfur atom, with the proviso that when n is 0, a compound wherein m is 1 and Y is a hydroxymethyl group is excluded and that when n is 0, a compound wherein Y is a group represented by $COOR^6$ ($R^6$ is a lower alkyl group) is excluded; or a pharmaceutically acceptable salt thereof.

With the oxazolidine derivative of the formula (I), optical isomers and geometrical isomers exist. The present invention includes these isomers and mixtures thereof.

The compounds of the formula (I) and pharmaceutically acceptable salts thereof according to the present invention have an activity to decrease blood triglyceride and cholesterol. These compounds have the features of being highly absorbable in the living body, having a long-sustained efficacy, and being excellent in the safety, the absorption and the excretion and less toxic. Thus the compounds are useful as drugs such as an anti-hyperlipidemic agent, an agent for preventing and treating arteriosclerosis, an anti-obesity agent and the like.

Thus the present invention provides an anti-hyperlipidemic composition, a composition for treating arteriosclerosis and a composition for treating obesity, each containing an effective amount of the compound of the formula (I) and a pharmaceutically acceptable carrier.

The present invention also provides a method of treating hyperlipidemia, arteriosclerosis or obesity, characterized by administering an effective amount of the compound of the formula (I) to a patient.

The invention further provides a process for preparing the compound of the formula (I).

Given below are specific examples of the groups as defined by $R^1$, $R^2$, $R^3$, $R^4$, $R^5$ and $R^6$, A, B, E and Y in the formula (I) and the groups described herein.

Examples of the lower alkyl group optionally having one or more halogen atoms are a lower alkyl group and a lower alkyl group having one or more halogen atoms.

Examples of the lower alkyl group are straight- or or branched-chain alkyl groups having 1 to 6 carbon atoms such as methyl, ethyl, n-propyl, isopropyl, n-butyl, iso-butyl, sec-butyl, tert-butyl, pentyl, iso-pentyl, hexyl and the like.

Examples of the lower alkyl group having one or more halogen atoms are straight- or branched-chain alkyl groups containing 1 to 6 carbon atoms and having 1 to 3 halogen atoms such as chloromethyl, bromomethyl, iodomethyl, fluoromethyl, dichloromethyl, dibromomethyl, difluoromethyl, trichloromethyl, tribromomethyl, trifluoromethyl, 2-chloroethyl, 2-bromoethyl, 2-fluoroethyl, 1,2-dichloroethyl, 2,2-difluoroethyl, 1-chloro-2-fluoroethyl, 2,2,2-trifluoroethyl, 2,2,2 -trichloroethyl, 3-fluoropropyl, 3,3,3-trichloropropyl, 4-chlorobutyl, 5-chloroheptyl, 6-chlorohexyl, 3-chloro-2-methylpropyl, etc.

Examples of the lower alkoxy group optionally having one or more halogen atoms are lower alkoxy groups or lower alkoxy groups having one or more halogen atoms.

Examples of the lower alkoxy group are straight- or branched-chain alkoxy groups having 1 to 6 carbon atoms such as methoxy, ethoxy, n-propoxy, iso-propoxy, n-butoxy, iso-butoxy, sec-butoxy, tert-butoxy, n-pentyloxy, iso-pentyloxy, n-hexyloxy, etc.

Examples of the lower alkoxy group having one or more halogen atoms are straight- or branched-chain lower alkoxy groups containing 1 to 6 carbon atoms and having 1 to 3 halogen atoms such as chloromethoxy, bromomethoxy, iodomethoxy, fluoromethoxy, dichloromethoxy, dibromomethoxy, difluoromethoxy, trichloromethoxy, tribromomethoxy, trifluoromethoxy, 2-chloroethoxy, 2-bromoethoxy, 2-fluoroethoxy, 1,2-dichloroethoxy, 2,2-difluoroethoxy, 1-chloro-2-fluoroethoxy, 2,2,2-trifluoroethoxy, 2,2,2-trichloroethoxy, 3-fluoropropoxy, 3,3,3-trichloropropoxy, 4-chlorobutoxy, 5-chlorohexoxy, 6-chlorohexyloxy, 3-chloro-2-methylpropyloxy, etc.

Examples of halogen atoms are fluorine, chlorine, bromine and iodine atoms.

Examples of the amino group optionally having one or more acetyl or lower alkyl groups are amino group, acetylamino group or an amino group having one or more lower alkyl groups.

The amino group having one or more lower alkyl groups is an amino group wherein one of the hydrogen atoms thereof is mono-substituted with any of the lower alkyl groups exemplified above or the two hydrogen atoms thereof are di-substituted with the same or different lower alkyl groups exemplified above, and includes, for example, an amino group having one or more straight- or branched-chain alkyl groups containing 1 to 6 carbon atoms, such as methylamino, ethylamino, n-propylamino, iso-propylamino, n-butylamino, tert-butylamino, pentylamino, hexylamino, dimethylamino, diethylamino, di-n-propylamino, di-isopropylamino, di-n-butylamino, di-tert-butylamino, dipentylamino, dihexylamino, methylethylamino, methyl n-propylamino, ethyl n-propylamino, ethyl n-butylamino, ethyl iso-butylamino, etc.

The lower alkoxycarbonyl group is an ester group of a carboxyl group with one of the alkyl groups as exemplified above, and includes, for example, a lower alkoxycarbonyl group containing a straight- or branched-chain alkoxy group having 1 to 6 carbon atoms, such as methoxycarbonyl, ethoxycarbonyl, n-propoxycarbonyl, iso-propoxycarbonyl, n-butoxycarbonyl, iso-butoxycarbonyl, sec-butoxycarbonyl, tert-butoxycarbonyl, n-pentyloxycarbonyl, iso-pentyloxycarbonyl, n-hexyloxycarbonyl, etc.

Examples of the lower alkanoyl group are straight- or branched-chain alkanoyl groups having 1 to 6 carbon atoms such as formyl, acetyl, propionyl, butyryl, isobutyryl, pentanoyl, hexanoyl, etc.

Examples of the alkylene chain $—(CH_2)_p—$ wherein p is 3, 4 or 5 are alkylene chains having 3 to 5 carbon atoms such as propylene, butylene, pentylene, etc.

Examples of the alkylenedioxy chain $—O(CH_2)_qO—$ wherein q is 1, 2 or 3 are alkylenedioxy chains having 1 to 3 carbon atoms such as methylenedioxy, ethylenedioxy, propylenedioxy, etc.

Examples of the lower alkylene group are straight- or branched-chain alkylene groups having 1 to 4 carbon atoms such as methylene, ethylene, trimethylene, tetramethylene, methylmethylene, 2-methyltrimethylene, etc.

Examples of the lower alkylene group which may be substituted with a halogen atom are lower alkylene groups or lower alkylene groups which are substituted with a halogen atom.

Examples of the lower alkylene group which is substituted with a halogen atom are straight- or branched-chain alkylene groups having 1 to 4 carbon atoms such as fluoromethylene, chloromethylene, bromomethylene, 1-chloroethylene, 2-chloroethylene, 1-bromoethylene, 2-bromoethylene, 2-chlorotrimethylene, 2-chlorotetramethylene, chloromethylmethylene, 2-chloromethyltrimethylene, etc.

Examples of the lower alkenylene group are straight- or branched-chain cis- or trans-alkenylene groups having 2 to 4 carbon atoms such as vinylene, 2-methylvinylene, propenylene, butenylene, etc.

The salt of the compound of the formula (I) include an acid addition salt or a basic salt prepared by causing a pharmaceutically acceptable acid or basic compound to act on the compound of the formula (I). Examples of the acid addition salt are salts of the compounds of the formula (I) having a basic group, especially an amino group, or a mono- or di-lower alkylamino group with an acid, such as an inorganic acid including hydrochloric acid, sulfuric acid, phosphoric acid, hydrobromic acid or the like, or an organic acid including oxalic acid, maleic acid, fumaric acid, malic acid, tartaric acid, citric acid, benzoic acid, acetic acid, p-toluenesulfonic acid, ethanesulfonic acid or the like. Examples of the basic salt include salts of the compounds of the formula (I) having an acidic group, especially carboxyl group with a base, e.g., salts of alkali metals such as sodium, potassium or the like or salts of alkaline earth metals such as magnesium, calcium or the like, and further include organic salts of the compounds of the formula (I) with amines such as ammonia, methylamine, dimethylamine, piperidine, cyclohexylamine, triethylamine or the like.

In the compound of the formula (I), m is 0 or 1, preferably m is 0;

n is 0 or 1, preferably n is 0;

B is bonded to the 4- or 5-position of the oxazolidine ring, preferably is bonded to the 5-position thereof;

Y is preferably a carboxyl group;

$R^4$ is preferably a hydrogen atom;

$R^5$ is preferably a hydrogen atom; and

Z is preferably an oxygen atom.

Preferred compounds are those wherein m and n are 0 and B is bonded to the 5-position of the oxazolidine ring.

Preferably, m is 0, B is attached to the 5-position of the oxazolidine ring, $R^4$ and $R^5$ represent a hydrogen atom, and Z is an oxygen atom. Preferably, m and n are 0, B is attached to the 5-position of the oxazolidine ring, $R^4$ and $R^5$ represent a hydrogen atom, and Z is an oxygen atom.

The oxazolidine derivatives of the formula (I) according to the present invention can be prepared from a variety of starting compounds, for example, by Processes A to F described below.

In the following processes, the compound wherein Y in its formula is a hydroxymethyl group or a carboxyl group can also be subjected to the reaction after protecting said group with a suitable protective group. Useful protective groups are not specifically limited insofar as the protective group does not produce adverse effect when the said protective group is removed by a deprotection reaction. For protecting a hydroxymethyl group, useful protective groups include methyl, ethyl and like lower alkyl groups, methoxymethyl, methoxyethyl and like lower alkoxyalkyl groups, tetrahydropyranyl, benzyl, trimethylsilyl, benzoyl and like acyl groups, and for protecting a carboxyl group, methyl, ethyl and like lower alkyl groups, benzyl and the like can be used.

When $R^1$, $R^2$ and $R^3$ represent a hydroxyl or carboxyl group in the formula of the compound, the compound can also be subjected to the reaction after protecting said group with a suitable protective group. Useful protective groups are not specifically limited insofar as the said protective group does not produce adverse effect when the protective group is removed by a deprotection reaction. For protecting a hydroxyl group, useful protective groups include methyl, ethyl and like lower alkyl groups, methoxymethyl, methoxyethyl and like lower alkoxyalkyl groups, tetrahydropyranyl, benzyl, trimethylsilyl, benzoyl and like acyl groups. For protecting a carboxyl group, methyl, ethyl and like lower alkyl groups, benzyl and the like can be used.

When $R^1$, $R^2$ and $R^3$ are a primary or secondary amino group which may have one or more lower alkyl groups, the compound in question may be subjected to the reaction after protecting said group with a suitable protective group. Useful protective groups are not specifically limited insofar as the said protective group does not produce adverse effect when the protective group is removed by a deprotection reaction. Usable as such protective groups are acetyl, benzoyl and like acyl groups, benzyl, Boc, Cbz and like urethane-type protective groups.

These protective groups can be deprotected by conventional methods.

compound of the formula (II) with the known compound of the formula (III) in a suitable solvent in the presence of a basic compound according to, for example, the process disclosed in Journal of Synthesis Organic Chemistry, Japan, 24, 60 (1966).

Useful solvents are not specifically limited insofar as they do not participate in the reaction. Examples of such solvents are diethyl ether, tetrahydrofuran, dioxane and like ethers, dichloromethane, chloroform and like halogenated hydrocarbons, pyridine, piperidine, triethylamine and like amines, acetone, methyl ethyl ketone, methyl isobutyl ketone and like alkyl ketones, methanol, ethanol, propanol and like alcohols, N,N-dimethylformamide, N,N-dimethylacetamide, acetonitrile, dimethylsulfoxide, hexamethylphosphoramide and like aprotic polar solvents, etc.

(Process A)

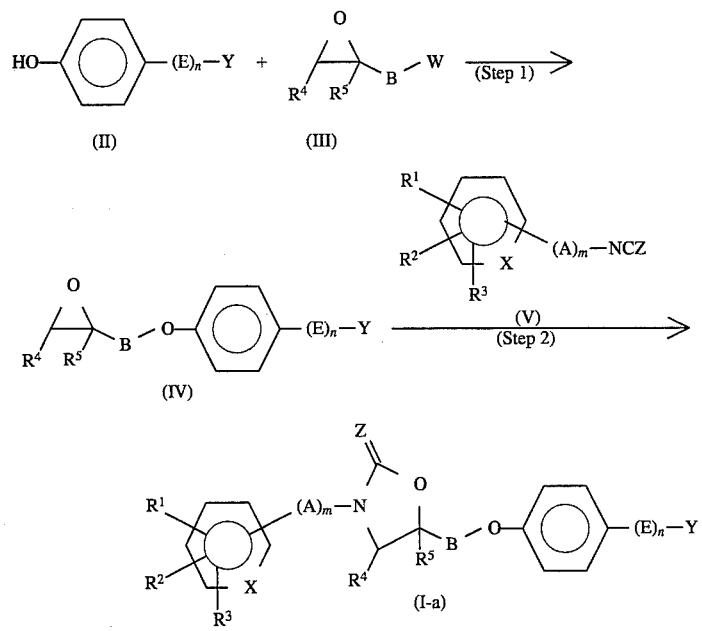

In the above formulas, $R^1$, $R^2$, $R^3$, $R^4$, $R^5$, A, B, E, X, Y, Z, m and n are as defined above, W is a halogen atom, an optionally substituted lower alkanesulfonyloxy group or an optionally substituted arylsulfonyloxy group.

In the compound of the formula (III), halogen atoms represented by W include the same atoms as exemplified above; and optionally substituted lower alkanesulfonyloxy groups are those having 1 to 6 carbon atoms which may be halogen-substituted, such as methanesulfonyloxy, ethanesulfonyloxy, propanesulfonyloxy, trifluoromethanesulfonyloxy and the like; optionally substituted arylsulfonyloxy groups include those which may be substituted with an alkyl group having 1 to 6 carbon atoms, a halogen atom or a nitro group, such as benzenesulfonyloxy, toluenesulfonyloxy, p-chlorobenzenesulfonyloxy, m-nitrobenzenesulfonyloxy and the like.

The steps in the above reaction scheme are carried out as described below in more detail.

(Step 1)

The compounds of the formula (IV), which in part include novel compounds, can be prepared by reacting the known Examples of the basic compounds are organic basic compounds such as triethylamine, pyridine and like tertiary amines, and inorganic basic compounds such as sodium carbonate, potassium carbonate and like alkali metal carbonates, sodium hydrogencarbonate, potassium hydrogencarbonate and like alkali metal hydrogencarbonates, sodium hydroxide, potassium hydroxide and like alkali metal hydroxides, sodium, potassium and like alkali metals, and sodium hydride and like alkali metal hydrides.

As to the proportions of the reactants, it is preferable that 1 to 2 mole equivalents of the compound of the formula (III), and 1 to 10 mole equivalents, preferably 1 to 3 mole equivalents, of the basic compound are used per mole of the compound of the formula (II). The reaction temperature is approximately 0° C. to the boiling point of the solvent, preferably 0° to 80° C. The reaction time is 0.5 to 48 hours, preferably 1 to 24 hours.

The compound of the formula (IV) prepared by the above reaction can be used in Step 2 after isolation or without isolation.

(Step 2)

The compounds of the formula (I-a) according to the invention can be prepared by reacting the compound of the formula (IV) with the known compound of the formula (V) in a suitable solvent in the presence of lithium bromide and tri-n-butylphosphine oxide.

Useful solvents are not specifically limited insofar as they do not participate in the reaction. Examples of the solvent are benzene, toluene, xylene and like aromatic hydrocarbons, diethyl ether, tetrahydrofuran, dioxane and like ethers, dichloromethane, chloroform and like halogenated hydrocarbons, acetone, methyl ethyl ketone, methyl isobutyl ketone and like alkyl ketones, N,N-dimethylformamide, N,N-dimethylacetamide, acetonitrile, dimethylsulfoxide and like aprotic polar solvents, etc.

As to the proportions of the reactants, it is preferable that 1 to 1.5 mole equivalents of the compound of the formula (V), and 0.01 to 0.3 mole equivalent, preferably 0.03 to 0.05 mole equivalent, of each of lithium bromide and tri-n-butylphosphine oxide are used per mole of the compound of the formula (IV). The reaction temperature is approximately 0° C. to the boiling point of the solvent, preferably 70° to 140° C. The reaction time is 0.1 to 6 hours, preferably 0.5 to 2 hours.

oxide.

Useful solvents are not specifically limited insofar as they do not participate in the reaction. Examples of solvents are benzene, toluene, xylene and like aromatic hydrocarbons, diethyl ether, tetrahydrofuran, dioxane and like ethers, dichloromethane, chloroform and like halogenated hydrocarbons, N,N-dimethylformamide, N,N-dimethylacetamide, acetonitrile, dimethylsulfoxide and like aprotic polar solvents, etc.

As to the proportions of the reactants, it is preferable that 1 to 1.5 mole equivalents of the compound of the formula (III), and 0.01 to 0.3 mole equivalent, preferably 0.03 to 0.05 mole equivalent, of each of lithium bromide and tri-n-butylphosphine oxide are used per mole of the compound of the formula (V). The reaction temperature is approximately 0° C. to the boiling point of the solvent, preferably 70° to 140° C. The reaction time is 0.1 to 6 hours, preferably 0.5 to 3 hours.

The compound of the formula (VI) prepared by the above reaction can be used in Step 2 after isolation or without isolation.

(Step 2)

The compound of the formula (I-a) according to the invention can be prepared by reacting the compound of the

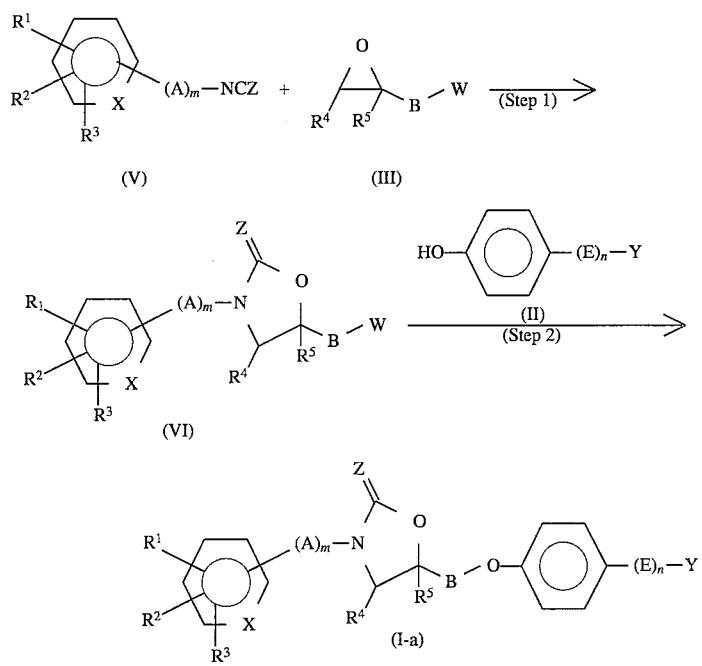

(Process B)

In the above formulas, $R^1$, $R^2$, $R^3$, $R^4$, $R^5$, A, B, E, W, X, Y, Z, m and n are as defined above.

The steps in the above reaction scheme are carried out as described below in more detail.

(Step 1)

The compound of the formula (VI) can be prepared by reacting the known compound of the formula (V) with the known compound of the formula (III) in a suitable solvent in the presence of lithium bromide and tri-n-butylphosphine formula (VI) with the compound of the formula (II) in a suitable solvent in the presence of a basic compound.

Useful solvents are not specifically limited insofar as they do not participate in the reaction. Examples of the solvent are benzene, toluene, xylene and like aromatic hydrocarbons, N,N-dimethylformamide, N,N-dimethylacetamide, acetonitrile, dimethylsulfoxide and like aprotic polar solvents, diethyl ether, tetrahydrofuran, dioxane and like ethers, methanol, ethanol, propanol and like alcohols, dichloromethane, chloroform and like halogenated hydrocarbons, pyridine, piperidine, triethylamine and like amines, acetone, methyl ethyl ketone, methyl isobutyl ketone and like alkyl ketones, etc.

Examples of the basic compounds are organic basic compounds such as triethylamine, pyridine and like tertiary amines, and inorganic basic compounds such as sodium carbonate, potassium carbonate and like alkali metal carbonates, sodium hydrogencarbonate, potassium hydrogencarbonate and like alkali metal hydrogencarbonates, sodium hydroxide, potassium hydroxide and like alkali metal hydroxides, sodium, potassium and like alkali metals, sodium hydride and like alkali metal hydrides and so on.

As to the proportions of the reactants, it is preferable that 1 to 1.5 mole equivalents of the compound of the formula (VI), and 1 to 10 mole equivalents, preferably 1 to 3 mole equivalents, of the basic compound are used per mole of the compound of the formula (II). The reaction temperature is approximately 0° C. to the boiling point of the solvent, preferably 0° to 80° C. The reaction time is 0.5 to 48 hours, preferably 2 to 12 hours.

The compound of the formula (I-a) obtained by (Process A) or (Process B) wherein Y is $COOR^6$ ($R^6$ is a lower alkyl group or a benzyl group) is subjected to hydrolysis or to catalytic reduction by a known conventional method, giving the compound of the present invention wherein $R^6$ is a hydrogen atom.

For example, the hydrolysis reaction is conducted in a suitable inert solvent by causing the acidic compound or basic compound to act on the compound of the formula (I-a).

Useful solvents are not specifically limited insofar as they do not participate in the reaction. Examples of the solvent are dimethyl ether, diethyl ether, tetrahydrofuran, dioxane, anisole and like ethers, dichloromethane, chloroform and like halogenated hydrocarbons, benzene, toluene, xylene and like aromatic hydrocarbons, pyridine, piperidine, triethylamine and like amines, hexane, heptane, octane and like aliphatic hydrocabons, methanol, ethanol, propanol and like alcohols, methyl acetate, ethyl acetate, and like acetic acid esters, N,N-dimethylformamide, N,N-dimethylacetamide, acetonitrile, dimethylsulfoxide, hexamethylphosphoramide and like aprotic polar solvents, carbon disulfide, acetic acid, water, mixtures of water and these organic solvents and so on.

Examples of acidic compounds are anhydrous aluminum chloride, stannic chloride, titanium tetrachloride, boron trichloride, boron trifluoride-ethyl ether complex, zinc chloride and like Lewis acids, hydrochloric acid, nitric acid, sulfuric acid and like inorganic acids, trichloroacetic acid, trifluoroacetic acid, methanesulfonic acid, acetic acid and like organic acids, acid-type ion-exchange resins and so on. Examples of basic compounds are organic basic compounds such as triethylamine, tributylamine and like trialkylamines, pyridine, picoline, 1,5-diazabicyclo[4,3,0]nonene-5 (DBN), 1,8-diazabicyclo[5,4,0]undecene-7 (DBU), 7,4-diazabicyclo[2,2,2]octane (DABCO) and the like, and inorganic basic compounds such as sodium carbonate, potassium carbonate and like alkali metal carbonates, sodium hydrogencarbonate, potassium hydrogencarbonate and like alkali metal hydrogencarbonates, sodium hydroxide, potassium hydroxide and like alkali metal hydroxides, sodium, potassium and like alkali metals, sodium hydride and like alkali metal hydrides and the like. It is recommended that the above acidic compound or basic compound is used in an amount of about 1 to about 100 mole equivalents, preferably about 1 to about 20 mole equivalents, per mole of the compound of the formula (I-a). Said reaction is carried out at about −20° to about 150° C., preferably −10° to 120° C. for about 0.5 to about 48 hours, preferably 1 to 24 hours.

The catalytic reduction is performed in an inert solvent in the presence of a catalyst. Useful solvents are not specifically limited insofar as they do not participate in the reaction. For example, ethyl acetate, methanol, tetrahydrofuran, dimethylformamide, acetic acid and the like can be used alone or in combination. Useful catalysts include, for example, palladium carbon, platinum, and so on. For the reaction, it is desired that 0.01 to 2 g, preferably 0.1 to 0.5 g, of the catalyst is used per gram of the compound of the formula (I-a). The hydrogen pressure ranges from atmospheric pressure to 3 atms., preferably atmospheric pressure to 2 atms. The reaction temperature is 0° to about 100° C., preferably room temperature to 70° C. The reaction time is 0.5 to 12 hours, preferably 1 to 4 hours.

The compound of the formula (I-a) obtained by (Process A) or (Process B) wherein Y is $COOR^6$ ($R^6$ is a hydrogen atom, a lower alkyl group or a benzyl group) is subjected to reduction by a known conventional method, giving the compound of the present invention wherein Y is a hydroxymethyl group. Stated more specifically, the compound is obtained by reduction in an inert solvent in the presence of lithium aluminum hydride or the like.

Useful solvents are not specifically limited insofar as they do not participate in the reaction. Examples of the solvent are tetrahydrofuran, dioxane, diethyl ether and so on. These solvents can be used alone or in combination. As to the proportions of the reactants, it is preferred that 0.5 to 3 mole equivalents of lithium aluminum hydride is used per mole of the compound of the formula (I-a). The reaction temperature is 0° to 100° C., preferably 0° to 50° C. The reaction time is 0.1 to 24 hours, preferably 0.5 to 6 hours.

Using an optically active compound of the formula (III) in Process A and Process B, an optically active oxazolidine derivative of the formula (I-a) according to the invention can be prepared. An optically active compound can be produced from a racemate in a conventional manner.

(Process C)

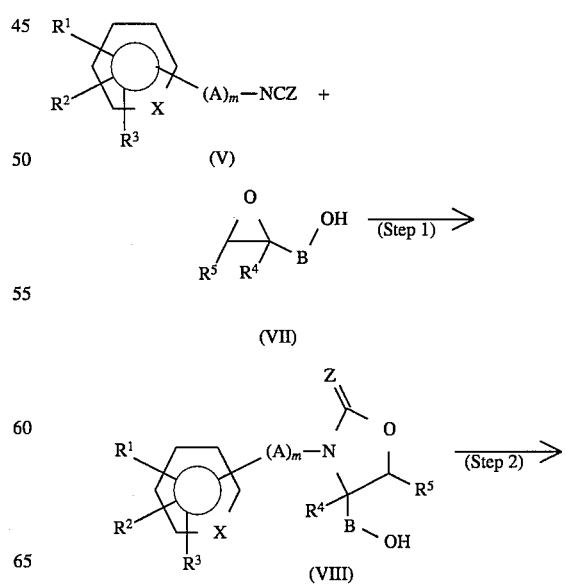

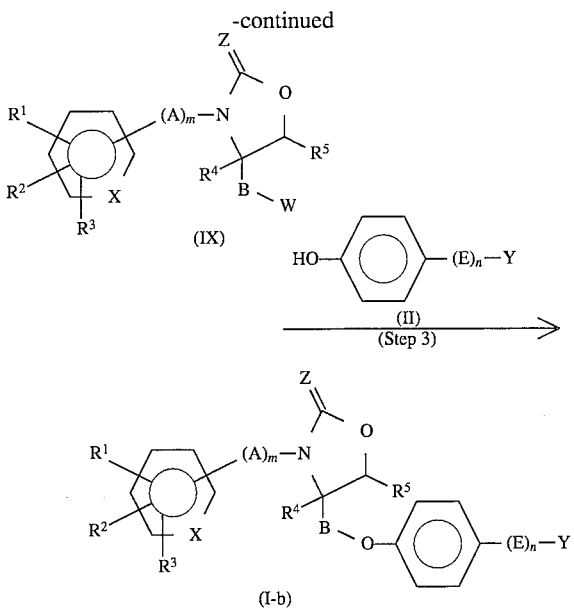

In the above formulas $R^1$, $R^2$, $R^3$, $R^4$, $R^5$, A, B, E, W, X, Y, Z, m and n are as defined above.

The steps in the above reaction scheme are carried out as described below in more detail.

(Step 1)

The compounds of the formula (VIII), which in part include novel compounds, can be prepared by reacting the known compounds of the formulas (V) and (VII) in an inert solvent in the presence of triethylamine according to, for example, the process disclosed in Chemistry Letter, 1991, 1245.

Useful solvents are not specifically limited insofar as they do not participate in the reaction. Examples of the solvent are benzene, toluene, xylene and like aromatic hydrocarbons, diethyl ether, tetrahydrofuran, dioxane and like ethers, dichloromethane, chloroform and like halogenated hydrocarbons, acetone, methyl ethyl ketone, methyl isobutyl ketone and like alkyl ketones, N,N-dimethylformamide, N,N-dimethylacetamide, acetonitrile, dimethylsulfoxide and like aprotic polar solvents, etc.

As to the proportions of the reactants, it is preferred that 1 to 1.5 mole equivalents of the compound of the formula (VII), and 0.5 to 10 mole equivalents, preferably 1 to 3 mole equivalents, of triethylamine are used per mole of the compound of the formula (V). The reaction temperature is approximately 0° C. to the boiling point of the solvent, preferably 0° to 80° C. The reaction time is 0.5 to 48 hours, preferably 2 to 24 hours.

The compound of the formula (VIII) prepared by the above reaction can be used in Step 2 after isolation or without isolation.

(Step 2)

The compound of the formula (IX) can be prepared by reacting the compound of the formula (VIII) with a halogenating agent, an alkanesulfonyl chloride having 1 to 6 carbon atoms which may be halogen-substituted or an optionally substituted arylsulfonyl chloride in an inert solvent in the presence or absence of an organic basic compound.

The reaction is carried out in a suitable solvent. Useful solvents are not specifically limited insofar as they do not participate in the reaction. Examples of the solvent are benzene, toluene, xylene and like aromatic hydrocarbons, triethyl amine, pyridine and like tertiary amines, diethyl ether, tetrahydrofuran, dioxane and like ethers, dichloromethane, chloroform and like halogenated hydrocarbons, N,N-dimethylformamide, N,N-dimethylacetamide, acetonitrile, dimethylsulfoxide and like aprotic polar solvents, etc.

Examples of the organic basic compounds are triethylamine, pyridine and like tertiary amines. Useful halogenating agents include, for example, thionyl chloride, phosphorus oxychloride, phosphorus pentachloride, phosphorus tribromide, etc. Examples of the alkanesulfonyl chloride having 1 to 6 carbon atoms which may be halogen-substituted or optionally substituted arylsulfonyl chloride are methanesulfonyloxy chloride, ethanesulfonyloxy chloride, propanesulfonyloxy cloride, trifluoromethanesulfonyloxy chloride, benzene sulfonyloxy chloride, toluenesulfonyloxy chloride, p-chlorobenzenesulfonyloxy chloride, m-nitrobenzenesulfonyloxy chloride, etc.

As to the proportions of the reactants, it is preferred that 1 to 3 mole equivalents of the organic basic compound, and 1 to 2 mole equivalents of the halogenating agent, alkanesulfonyl chloride having 1 to 6 carbon atoms which may be halogen-substituted or optionally substituted arylsulfonyl chloride are used per mole of the compound of the formula (VIII). The reaction temperature is approximately 0° C. to the boiling point of the solvent, preferably 0° to 100° C. The reaction time is 0.1 to 24 hours, preferably 0.5 to 3 hours.

The compound of the formula (IX) prepared by the above reaction can be used in Step 3 after isolation or without isolation.

(Step 3)

The compound of the formula (I-b) according to the invention can be prepared by reacting the compound of the formula (IX) with the known compound of the formula (II) in a suitable solvent in the presence of a basic compound.

Useful solvents are not specifically limited insofar as they do not participate in the reaction. Examples of solvents are diethyl ether, tetrahydrofuran, dioxane and like ethers, dichloromethane, chloroform and like halogenated hydrocarbons, pyridine, piperidine, triethylamine and like amines, acetone, methyl ethyl ketone, methyl isobutyl ketone and like alkyl ketones, methanol, ethanol, propanol and like alcohols, N,N-dimethylformamide, N,N-dimethylacetamide, acetonitrile, dimethylsulfoxide, hexamethylphosphoramide and like aprotic polar solvents, etc.

Examples of the basic compounds are organic basic compounds such as triethylamine, pyridine and like tertiary amines, and inorganic basic compounds such as sodium carbonate, potassium carbonate and like alkali metal carbonates, sodium hydrogencarbonate, potassium hydrogencarbonate and like alkali metal hydrogencarbonates, sodium hydroxide, potassium hydroxide and like alkali metal hydroxides, sodium, potassium and like alkali metals, sodium hydride and like alkali metal hydrides and so on.

As to the proportions of the reactants, it is desirable that 1 to 2 mole equivalents of the compound of the formula (II), and 1 to 5 mole equivalents, preferably 1 to 2 mole equivalents, of the basic compound are used per mole of the compound of the formula (IX). The reaction temperature is approximately 0° C. to the boiling point of the solvent, preferably 0° to 80° C. The reaction time is 0.5 to 48 hours, preferably 1 to 8 hours.

The compound of the formula (I-b) obtained by (Process C) wherein Y is COOR$^6$ (R$^6$ is a lower alkyl group or a benzyl group) is subjected to hydrolysis or to catalytic reduction by a known conventional method, giving the compound of the present invention wherein Y is a hydrogen atom. Additionally the compound of the invention wherein Y is a hydroxymethyl group can be prepared by reducing the compound of the formula (I-b) wherein Y is COOR$^6$ (R$^6$ is a hydrogen atom, a lower alkyl group or a benzyl group) by a known conventional method. For example, the compound can be prepared by the same method as used for preparing the compound of the formula (I-a).

Using an optically active compound of the formula (VII) in this process, an optically active oxazolidine derivative of the formula (I-b) according to the invention can be prepared. An optically active compound can be produced from a racemate in a conventional manner.

Some of the compounds according to the invention can be prepared by other processes given below, i.e. Processes D to F.

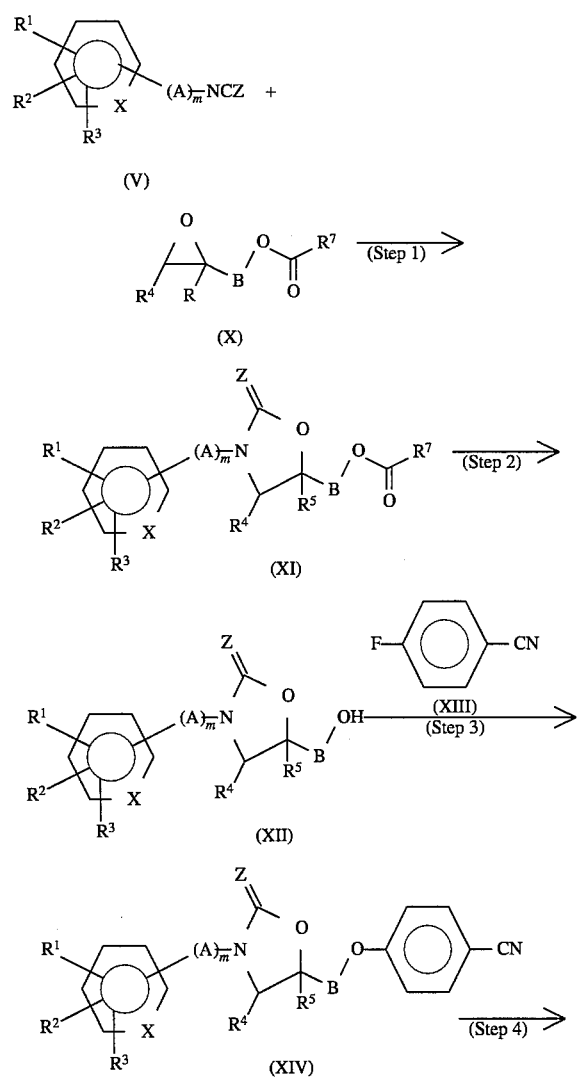

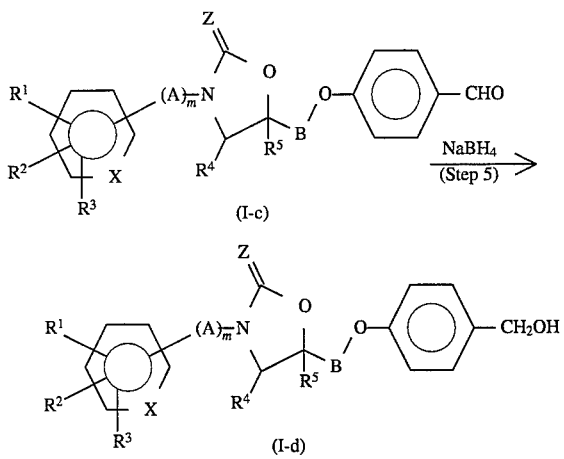

In the above formulas, R$^1$, R$^2$, R$^3$, R$^4$, R$^5$, A, B, X, Z and m are as defined above, and R$^7$ is an optionally substituted lower alkyl group or an optionally substituted aryl group.

Examples of optionally substituted lower alkyl groups are alkyl groups having 1 to 6 carbon atoms which may be halogen-substituted, such as methyl, ethyl, propyl, trifluoromethyl and the like. Examples of optionally substituted aryl groups are aryl groups which may be substituted with an alkyl group having 1 to 6 carbon atoms, a halogen atom or a nitro group, such as phenyl, tolyl, p-chlorophenyl, p-nitrophenyl and the like.

The steps in the above reaction scheme are carried out as described below in more detail.

(Step 1)

The compound of the formula (XI) can be prepared by reacting the known compound of the formula (V) with the known compound of the formula (X) in a suitable solvent in the presence of lithium bromide and tri-n-butylphosphine oxide.

Useful solvents are not specifically limited insofar as they do not participate in the reaction. Examples of the solvent are benzene, toluene, xylene and like aromatic hydrocarbons, diethyl ether, tetrahydrofuran, dioxane and like ethers, dichloromethane, chloroform and like halogenated hydrocarbons, acetone, methyl ethyl ketone, methyl isobutyl ketone and like alkyl ketones, N,N-dimethylformamide, N,N-dimethylacetamide, acetonitrile, dimethylsulfoxide and like aprotic polar solvents, etc.

As to the proportions of the reactants, it is desirable that 1 to 1.5 mole equivalents of the compound of the formula (V), and 0.01 to 0.3 mole equivalent, preferably 0.03 to 0.05 mole equivalent, of each of lithium bromide and tri-n-butylphosphine oxide are used per mole of the compound of the formula (X). The reaction temperature is approximately 0° C. to the boiling point of the solvent, preferably 70° to 140° C. The reaction time is 0.1 to 6 hours, preferably 0.5 to 2 hours.

The compound of the formula (XI) prepared by the above reaction can be used in Step 2 after isolation or without isolation.

(Step 2)

The compound of the formula (XII) can be prepared by a conventional hydrolysis by causing an acidic compound or a basic compound to act on the compound of the formula (XI) in a suitable inert solvent.

Useful solvents are not specifically limited insofar as they do not participate in the reaction. Examples of the solvent are diethyl ether, tetrahydrofuran, dioxane, anisole and like ethers, dichloromethane, chloroform and like halogenated hydrocarbons, benzene, toluene, xylene and like aromatic hydrocarbons, pyridine, piperidine, triethylamine and like amines, hexane, heptane, octane and like aliphatic hydrocarbons, acetone, methyl ethyl ketone, methyl isobutyl ketone and like alkyl ketones, methanol, ethanol, propanol and like alcohols, methyl acetate, ethyl acetate and like acetic acid esters, N,N-dimethylformamide, N,N-dimethylacetamide, acetonitrile, dimethylsulfoxide, hexamethylphosphoric acid triamide and like aprotic polar solvents, carbon disulfide, acetic acid, water, mixtures of water and these organic solvents and so on.

Examples of the acidic compound are anhydrous aluminum chloride, stannic chloride, titanium tetrachloride, boron trichloride, boron trifluoride-ethyl ether complex, zinc chloride and like Lewis acids, hydrochloric acid, nitric acid, sulfuric acid and like inorganic acids, trichloroacetic acid, trifluoroacetic acid, methanesulfonic acid, acetic acid and like organic acids, acid-type ion-exchange resins and so on.

Examples of the basic compound are organic basic compounds such as triethylamine, pyridine and like tertiary amines, and inorganic basic compounds such as sodium carbonate, potassium carbonate and like alkali metal carbonates, sodium hydrogencarbonate, potassium hydrogencarbonate and like alkali metal hydrogencarbonates, sodium hydroxide, potassium hydroxide and like alkali metal hydroxides, sodium, potassium and like alkali metals, sodium hydride and like alkali metal hydrides and so on.

As to the proportions of the reactants, it is desirable that 1 to 100 mole equivalents, preferably 1 to 20 mole equivalents, of the acidic compound or basic compound, is used per mole of the compound of the formula (XI). The reaction temperature is −20° C. to the boiling point of the solvent, preferably −10° to 120° C. The reaction time is 0.5 to 48 hours, preferably 1 to 24 hours.

The compound of the formula (XII) prepared by the above reaction can be used in Step 3 after isolation or without isolation.

(Step 3)

The compound of the formula (XIV) can be prepared by reacting the compound of the formula (XII) with p-fluorobenzonitrile of the formula (XIII) in a suitable solvent in the presence of a basic compound.

Useful solvents are not specifically limited insofar as they do not participate in the reaction. Examples of the solvent are diethyl ether, tetrahydrofuran, dioxane and like ethers, dichloromethane, chloroform and like halogenated hydrocarbons, pyridine, piperidine, triethylamine and like amines, acetone, methyl ethyl ketone, methyl. isobutyl ketone and like alkyl ketones, methanol, ethanol, propanol and like alcohols, N,N-dimethylformamide, N,N-dimethylacetamide, acetonitrile, dimethylsulfoxide, hexamethylphosphoramide and like aprotic polar solvents, etc.

Examples of the basic compound are organic basic compounds such as triethylamine, pyridine and like tertiary amines, and inorganic basic compounds such as sodium carbonate, potassium carbonate and like alkali metal carbonates, sodium hydrogencarbonate, potassium hydrogencarbonate and like alkali metal hydrogencarbonates, sodium hydroxide, potassium hydroxide and like alkali metal hydroxides, sodium, potassium and like alkali metals, sodium hydride and like alkali metal hydrides and so on.

As to the proportions of the reactants, it is desirable that 1 to 2 mole equivalents of p-fluorobenzonitrile of the formula (XIII), and 1 to 5 mole equivalents, preferably 1 to 2 mole equivalents, of the basic compound are used per mole of the compound of the formula (XII). The reaction temperature is approximately 0° C. to the boiling point of the solvent, preferably 0° to 80° C. The reaction time is 0.5 to 48 hours, preferably 1 to 8 hours.

The compound of the formula (XIV) prepared by the above reaction can be used in Step 4 after isolation or without isolation.

(Step 4)

The compound of the formula (I-c) can be prepared by causing a Raney nickel to act on the compound of the formula (XIV) in a suitable inert solvent.

Useful solvents are not specifically limited insofar as they do not participate in the reaction. Examples of solvents are formic acid, acetic acid, water, mixtures of water and these organic solvents, etc.

As to the proportions of the reactants, it is desirable that 0.5 to 10 g, preferably 1 to 3 g, of the Raney nickel is used per gram of the compound of the formula (XIV). The reaction temperature is approximately 0° C. to the boiling point of the solvent, preferably 50° to 100° C. The reaction time is 0.5 to 12 hours, preferably 1 to 3 hours.

The compound of the formula (I-c) prepared by the above reaction, which per se has an activity to reduce the lipid content in the blood, can be used in Step 5 as an intermediate after isolation or without isolation.

(Step 5)

The compound of the formula (I-d) according to the invention can be prepared by reducing the compound of the formula (I-c) in an inert solvent in the presence of sodium boron hydride or the like.

Useful solvents are not specifically limited insofar as they do not participate in the reaction. Examples of solvents are tetrahydrofuran, dioxane, diethyl ether and like ethers, methanol, ethanol, propanol and like alcohols, etc. These solvents can be used alone or in combination. As to the proportions of the reactants, it is desirable that 0.5 to 3 mole equivalents of sodium boron hydride is used per mole of the compound of the formula (I-c). The reaction temperature is 0° to 100° C., preferably 0° to 50° C. The reaction time is 0.1 to 24 hours, preferably 0.5 to 6 hours.

Using an optically active compound of the formula (X) in this process, an optically active oxazolidine derivatives of the formulas (I-c) and (I-d) according to the invention can be prepared. An optically active compound can be produced from a racemate in a conventional manner.

(Process E)

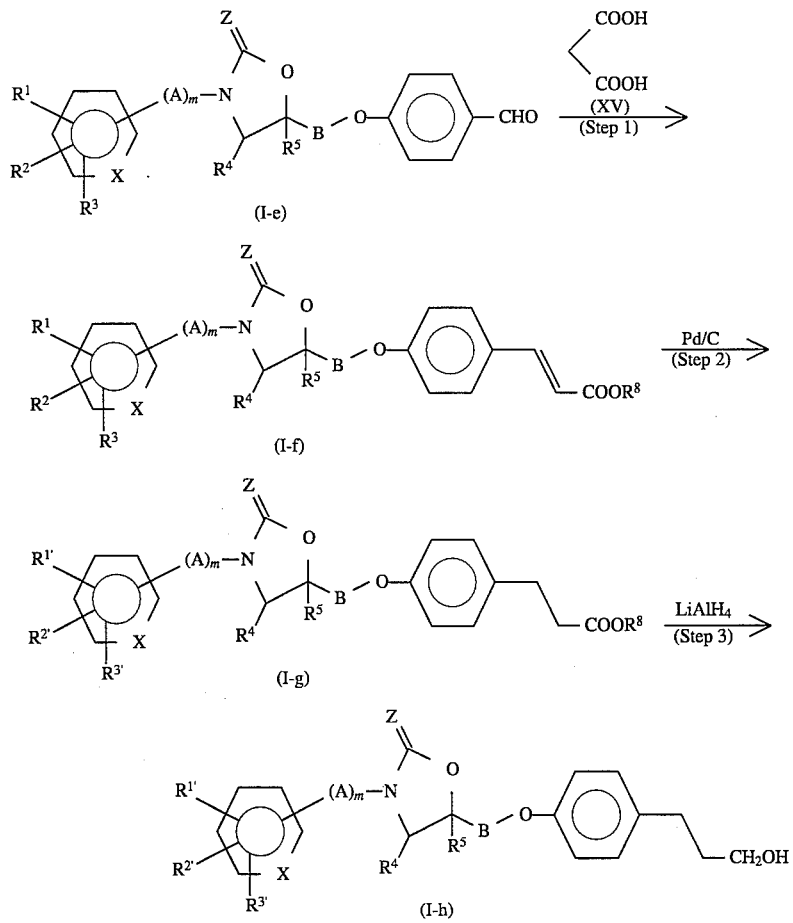

In the above formulas, $R^1$, $R^2$, $R^3$, $R^4$, $R^5$, A, B, X, Z and m are as defined above, $R^{1'}$, $R^{2'}$ or $R^{3'}$ are the same as $R^1$, $R^2$, $R^3$ except that they are other than a nitro group or a nitrile group, and $R^8$ is a lower alkyl group.

The steps in the above reaction scheme are carried out as described below in more detail.

(Step 1)

The compound of the formula (I-f) according to the invention can be prepared by reacting the compound of the formula (I-e) (identical with the compound of the formula (I-c)) with a malonic acid of the formula (XV) in a suitable solvent in the presence of the basic compound and subsequently esterifying the obtained carboxylic acid compound by the Fischer esterification method as described, for example, in Org. Synth. Coll., vol. 2, 414 (1943).

Useful solvents are not specifically limited insofar as they do not participate in the reaction. Examples of solvents are benzene, toluene, xylene and like aromatic hydrocarbons, triethylamine, pyridine and like tertiary amines, diethyl ether, tetrahydrofuran, dioxane, dimethoxyethane and like ethers, methanol, ethanol, propanol, 2-propanol, butanol and like alcohols, N,N-dimethylformamide, N,N-dimethylacetamide, acetonitrile, dimethylsulfoxide, hexamethylphosphoric acid triamide and like aprotic polar solvents, etc.

Examples of the basic compound are organic basic compounds such as sodium acetate, potassium acetate and like alkali metal fatty acid salts, triethylamine, pyridine and like tertiary amines, piperidine and the like, and inorganic basic compounds such as sodium carbonate, potassium carbonate and like alkali metal carbonates, sodium hydrogencarbonate, potassium hydrogencarbonate and like alkali metal hydrogencarbonates, sodium, potassium and like alkali metals, sodium hydride and like alkali metal hydrides and the like.

As to the proportions of the reactants, it is desirable that 1 to 3 mole equivalents of the malonic acid of the formula (XV), and 0.05 to 50 mole equivalents, preferably 0.1 to 10 mole equivalents, of the basic compound are used per mole of the compound of the formula (I-e). The reaction temperature is approximately 0° C. to the boiling point of the solvent, preferably 80° to 120° C. The reaction time is 0.5 to 48 hours, preferably 1 to 12 hours.

Further, the carboxylic acid compound thus obtained (compound of the invention) is esterified in a suitable solvent in the presence of an acid catalyst to thereby obtain an ester compound. The solvent is suitably selected depending on the desired ester and includes, for example, methanol, ethanol, propanol and like alcohols. Useful acid catalysts include, for example, hydrochloric acid, sulfuric acid and like inorganic acids, etc. As to the proportions of the reactants, it is desirable that 0.01 to 1 ml, preferably 0.1 to 0.5 ml, of the acid catalyst is used per gram of the carboxylic acid compound. The reaction temperature is approximately 0° C. to the boiling point of the solvent, preferably 20° to 100° C. The reaction time is 0.5 to 48 hours, preferably 2 to 24 hours.

The compound of the formula (I-f) per se has an activity to reduce the lipid content in the blood and can be used in Step 2 as an intermediate after isolation or without isolation.

(Step 2)

The compound of the formula (I-g) according to the invention is produced by subjecting the compound of the formula (I-f) to catalytic reduction in an inert solvent in the presence of a catalyst.

Useful solvents are not specifically limited insofar as they do not participate in the reaction. Examples of the solvent are ethyl acetate, methanol, tetrahydrofuran, dioxane, N,N-dimethylformamide, acetic acid, etc. These solvents can be used alone or in combination. Useful catalysts include palladium carbon, platinum, etc. As to the proportions of the reactants, it is desirable that 0.01 to 2 g, preferably 0.1 to 0.5 g, of the catalyst is used per gram of the compound of the formula (I-f). The hydrogen pressure is in the range of atmospheric pressure to 20 atms. The reaction temperature is approximately 0° to 100° C., preferably room temperature to 50° C. The reaction time is 0.5 to 24 hours, preferably 1 to 8 hours.

The compound of the formula (I-g) prepared by the above reaction per se has an activity to reduce the lipid content in the blood and can be used in Step 3 as an intermediate after isolation or without isolation.

(Step 3)

The compound of the formula (I-h) according to the invention can be prepared by subjecting the compound of the formula (I-g) to reduction in an inert solvent in the presence of lithium aluminum hydride or the like.

Useful solvents are not specifically limited insofar as they do not participate in the reaction. Examples of the solvent are tetrahydrofuran, dioxane, diethyl ether and so on. These solvents can be used alone or in combination. As to the proportions of the reactants, it is desirable that 0.5 to 3 mole equivalents of lithium aluminum hydride is used per mole of the compound of the formula (I-h). The reaction temperature is 0° to 100° C., preferably 0° to 50° C. The reaction time is 0.1 to 24 hours, preferably 0.5 to 6 hours.

Using an optically active compound of the formula (I-e) in this process, an optically active oxazolidine derivatives of the formulas (I-f) to (I-h) according to the invention can be prepared. An optically active compound can be produced from a racemate in a conventional manner.

(Process F)

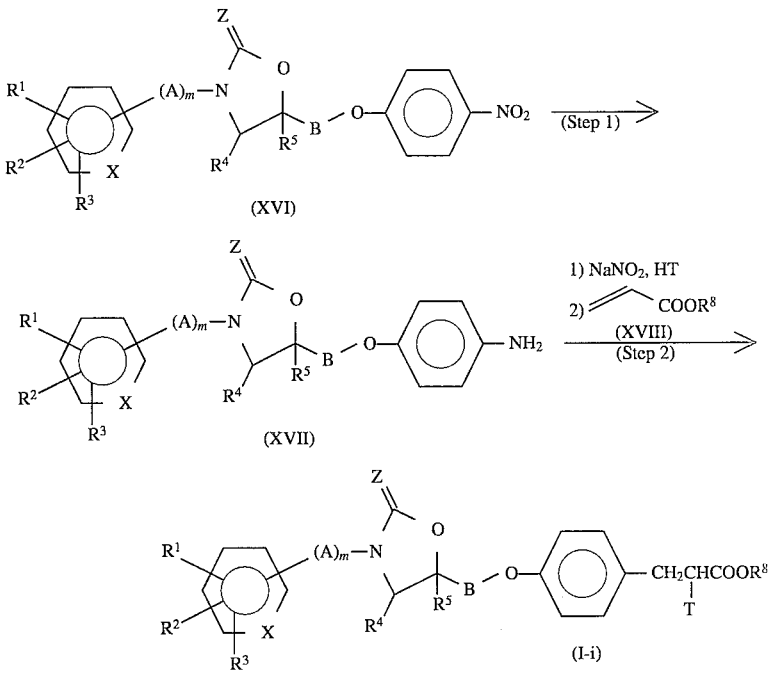

In the above reaction scheme, $R^1$, $R^2$, $R^3$, $R^4$, $R^5$, $R^8$, A, B, X, Z and m are as defined above (except for a compound wherein $R^1$, $R^2$ or $R^3$ is a nitro group), and T is a halogen atom.

The steps in the above reaction scheme are carried out as described below in more detail.

(Step 1)

The compound of the formula (XVII) can be prepared by subjecting the known compound of the formula (XVI) to catalyst reduction in an anert solvent in the presence of a catalyst. The compound of the formula (XVI) can be prepared by reacting N-aryl urethane with p-nitrophenyl glycidyl ether as disclosed, for example, in Journal of Synthesis Organic Chemistry, Japan, 24, 60 (1966).

Useful solvents are not specifically limited insofar as they do not participate in the reaction. For example, ethyl actate, methanol, tetrahydrofuran, dioxane, N,N-dimethylformamide, acetic acid and the like can be used alone or in combination. Useful catalysts include, for example, palladium carbon, platinum, etc.

As to the proportions of the reactants, it is desirable that 0.01 to 2 g, preferably 0.1 to 0.5 g, of the catalyst is used per gram of the compound of the formula (XVI). The hydrogen pressure ranges from atmospheric pressure to 100 atms., preferably atmospheric pressure to 20 atms. The reaction temperature is 0° to 100° C., preferably room temperature to 60° C. The reaction time is 0.5 to 48 hours, preferably 2 to 24 hours.

The compound of the formula (XVII) prepared by the above reaction can be used in Step 2 after isolation or without isolation.

(Step 2)

The compound of the formula (I-i) can be prepared by diazotizing the compound of the formula (XVII) in a suitable solvent in the presence of a hydrogen halide (HT) using sodium nitrite and then reacting the obtained compound with acrylic acid ester of the formula (XVIII) in the presence of cuprous oxide.

Useful solvents are not specifically limited insofar as they do not participate in the reaction. Examples of the solvent are diethyl ether, tetrahydrofuran, dioxane and like ethers, acetone, methyl ethyl ketone, methyl isobutyl ketone and like alkyl ketones, methanol, ethanol, propanol and like alcohols, N,N-dimethylformamide, N,N-dimethylacetamide, acetonitrile, dimethylsulfoxide, hexamethylphosphoric acid triamide and like aprotic polar solvents, water, acetic acid, etc. These solvents can be used alone or in combination.

As to the proportions of the reactants, it is desirable that 1 to 50 mole equivalents of the hydrogen halide (HT), 1 to 2 mole equivalents of sodium nitrite, 1 to 10 mole equivalents of the acrylic acid ester of the formula (XVIII), and 0.05 to 0.5 mole equivalent of the cuprous oxide are used per mole of the compound of the formula (XVII). The reaction temperature is approximately 0° C. to the boiling point of the solvent, preferably 0° to 50° C. The reaction time is 0.1 to 24 hours, preferably 0.5 to 3 hours.

Using an optically active compound of the formula (XV) in this process, an optically active oxazolidine derivative of the formula (I-i) according to the invention can be prepared. An optically active compound can be produced from a racemate in a conventional manner.

The compounds of the formula (I) according to the present invention prepared by any of Processes A to F can be isolated from the reaction product by a conventional separation technique such as column chromatography, recrystallization, distillation under reduced pressure, etc.

The salts of the compounds of the formulas (I-a), (I-b), (I-c), (I-d), (I-e), (I-f), (I-g), (I-h) and (I-i) can be easily produced by reacting each free compound with any of the above-exemplified acids or basic compounds by a conventional method.

For use as medicaments, the compounds of the present invention can be made into various pharmaceutical dosage forms according to a preventive or therapeutic purpose. Examples of pharmaceutical dosage forms are oral preparations, injections, suppositories, ointments, plasters and so on. Such preparations can be formulated in a manner already known and conventional to those skilled in the art.

For the formulation of solid preparations for oral administration, an excipient and, when required, a binder, disintegrator, lubricant, coloring agent, corrigent, flavor, etc. are added to the compound of the invention, and then a preparation is formulated in a conventional way as tablets, coated tablets, granules, powders, capsules or the like. Such additives are those already known in the art, and useful examples are excipients such as lactose, sucrose, sodium chloride, glucose, starch, calcium carbonate, kaolin, microcrystalline cellulose and silicic acid; binders such as water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; disintegrators such as dried starch, sodium alginate, agar powder, sodium hydrogencarbonate, calcium carbonate, sodium lauryl sulfate, stearic acid monoglyceride and lactose; lubricants such as purified talc, stearic acid salt, borax and polyethylene glycol; corrigents such as sucrose, bitter orange peel, citric acid and tartaric acid, etc.

For the formulation of liquid preparations for oral administration, a corrigent, buffer, stabilizer, flavor, etc. are added to the compound of the present invention, and the mixture can be formulated in a conventional way into an oral liquid preparation, syrup, elixir or the like. Examples of useful corrigents are those exemplified above. Examples of buffers are sodium citrate, etc. Examples of stabilizers are tragacanth, gum arabic, gelatin, etc.

Injections can be prepared as a subcutaneous, intramuscular or intravenous injection in a conventional way by adding to the compound of the invention a pH adjusting agent, buffer, stabilizer, isotonic agent, local anesthetic, etc. Examples of pH adjusting agents and buffers are sodium citrate, sodium acetate, sodium phosphate, etc. Examples of stabilizers are sodium pyrosulfite, EDTA, thioglycolic acid, thiolactic acid, etc. Examples of local anesthetics are procaine hydrochloride, lidocaine hydrochloride, etc. Examples of isotonic agents are sodium chloride, glucose, etc.

Suppositories can be prepared in a usual manner by adding to the compound of the invention a pharmaceutically acceptable carrier already known in the art, such as polyethylene glycols, lanolin, cacao fat and oil, fatty acid triglycerides and, if desired, a surfactant such as Tween (registered trademark).

For the preparation of ointments, a base, a stabilizer, a humectant, a preservative and the like commonly used in the art are used as required. These additives together with the compound of the present invention are formulated into ointments by conventional methods. Useful examples of the base include, for example, liquid paraffin, white petrolatum, bleached beeswax, octyl dodecyl alcohol, paraffin, etc. As preservatives, there can be mentioned methyl para-hydroxybenzoate, ethyl para-hydroxybenzoate, para-hydroxy propyl benzoate, etc.

For the preparation of plasters, said ointment, cream, gel or paste of the drug is applied to a substrate commonly employed in the art in a conventional manner. Suitable examples of substrates are woven or non-woven fabrics of cotton, rayon, chemical fibers or the like and films or foamed sheets of soft vinyl chloride, polyethylene, polyurethane or the like.

The amount of the compound of the present invention to be incorporated into each of the unit dosage forms varies with the symptoms of the patient or with the type of the preparations. The preferable amount per dosage unit is about 1 to about 1,000 mg for oral preparations, about 0.1 to about 500 mg for injections, or about 5 to about 1,000 mg for suppositories. The dosage per day of the drug in the above dosage forms is variable with the symptoms, body weight, age, sex and other factors of the patient, but usually ranges from about 0.1 to about 5,000 mg, preferably from about 1 to about 1,000 mg for human adult per day. The preparation is preferably administered in a single dose or in two to four divided doses.

EXAMPLES

Reference Examples and Examples are given below to illustrate the present invention in further detail.

Reference Example 1

Synthesis of (R)-(−)-4-(oxiranylmethoxy)-benzaldehyde

In 800 ml of anhydrous methyl ethyl ketone was dissolved 23.54 g of 4-hydroxybenzaldehyde and 50 g of (R)-(−)-glycidyl m-nitrobenzenesulfonate. To the solution was added 34.6 g of anhydrous potassium carbonate, and the mixture was refluxed with heating for 2.5 hours. The reaction mixture was filtered, and the filtrate was concentrated under reduced pressure. The obtained residue was extracted with ethyl acetate. The extract was washed with water, dried with magnesium sulfate and filtered, and the filtrate was concentrated under reduced pressure. The residue was subjected to silica gel column chromatography and purified with chloroform to give 30.6 g of the title compound (yield 89%).

Melting point: 32° C. Specific rotation: $[\alpha]_D^{25}=-5.83°$ (c=1.0, CHCl$_3$) NMR spectrum (CDCl$_3$) δ2.79 (1H, dd, J=7.4, 5.0 Hz), 2.94(1H, dd, J=5.0, 4.3 Hz), 3.39(1H, m), 4.02(1H, dd, J=11.2, 5.9 Hz), 4.35(1H, dd, J=11.2, 2.9 Hz), 7.03(2H, d, J=8.9 Hz), 7.85 (2H, d, J=8.9 Hz), 9.93(1H, s) MASS spectrum (EI) m/z 178 (M$^+$)

Reference Example 2

Synthesis of (S)-(+)-4-(oxiranylmethoxy)-benzaldehyde

The same procedure of Reference Example 1 was repeated except that (S)-(+)-glycidyl m-nitrobenzenesulfonate was used in lieu of (R)-(−)-glycidyl m-nitrobenzenesulfonate to give the title compound (yield 91%).

Melting point: 32° C. Specific rotation: $[\alpha]_D^{25}=+6.65°$ (c=1.0, CHCl$_3$) NMR spectrum (CDCl$_3$) δ 2.79 (1H, dd, J=7.4, 5.0 Hz), 2.94(1H, dd, J=5.0, 4.3 Hz), 3.39(1H, m), 4.02(1H, dd, J=11.2, 5.9 Hz), 4.35(1H, dd, J=11.2, 2.9 Hz), 7.03(2H, d, J=8.9 Hz), 7.85 (2H, d, J=8.9 Hz), 9.93(1H, s) MASS spectrum (EI) m/z 178 (M$^+$)

Reference Example 3

Synthesis of 4-(oxiranylethoxy)-benzaldehyde

The procedure of Reference Example 1 was repeated except that oxiranylethyl methanesulfonate was used in lieu of (R)-(−)-glycidyl m-nitrobenzenesulfonate to give the title compound as an oil (yield 78%).

NMR spectrum (CDCl$_3$) δ1.95 (1H, m), 2.20(1H, m), 2.60(1H, dd, J=5.0, 2.6 Hz), 2.85(1H, dd, J=5.0, 4.0 Hz), 3.16(1H, m), 4.20(2H, m), 7.01 (2H, d, J=8.9 Hz), 7.84(2H, d, J=8.9 Hz), 9.89(1H, s) MASS spectrum (FAB) 193 (M$^+$+1)

Reference Example 4

Synthesis of benzyl 4-(oxiranylmethoxy)-benzoate

In 120 ml of anhydrous N,N-dimethylformamide was dissolved 25.9 g of benzyl 4-hydroxybenzoate and 12.7 ml of epibromohydrin. To the solution was added 23.6 g of anhydrous potassium carbonate, and the mixture was stirred at 70° C. for 16 hours. The reaction mixture was concentrated under reduced pressure, and the obtained residue was extracted with ethyl acetate. The extract was washed with water, dried with magnesium sulfate and filtered. The filtrate was concentrated under reduced pressure. The residue was subjected to silica gel column chromatography and purified by hexane-ethyl acetate gradient elution to give 24.5 g of the title compound as an oil (yield 76%).

NMR spectrum (CDCl$_3$) δ2.77 (1H, dd, J=5.0, 2.6 Hz), 2.92(1H, dd, J=5.0, 4.3 Hz), 3.37(1H, dddd, J=5.8, 5.0, 4.3, 3.0, 2.6 Hz), 3.97(1H, dd, J=11.2, 5.8 Hz), 4.29(1H, dd, J=11.2, 3.0 Hz), 5.34 (2H, s), 6.93(2H, d, J=9.2 Hz), 7.3–7.5(5H, m), 8.03 (2H, d, J=9.2 Hz) MASS spectrum (EI) m/z 284(M$^+$)

Reference Example 5

Synthesis of methyl (R)-(−)-4-(oxiranylmethoxy)-benzoate

The same procedure of Reference Example 4 was repeated except that methyl 4-hydroxybenzoate was used in lieu of benzyl 4-hydroxybenzoate, and (R)-(−)-glycidyl toluenesulfonate was used in lieu of epibromohydrin to give the title compound (yield 90%).

Melting point: 34°–36° C. Specific rotation: $[\alpha]_D^{23}=-7.7°$ (c=1.0, CH$_2$Cl$_2$) NMR spectrum (CDCl$_3$) δ2.79 (1H, dd, J=5.0, 2.6 Hz), 2.93(1H, dd, J=5.0, 4.3 Hz), 3.38(1H, dddd, J=5.8, 5.0, 4.3, 3.0, 2.6 Hz), 3.89(3 H, s), 3.99(1H, dd, J=11.2, 5.8 Hz), 4.30 (1H, dd, J=11.2, 3.0 Hz), 6.94(2H, d, J=8.9 Hz), 7.99(2H, d, J=8.9 Hz)

| Elementary analysis: (for C$_{11}$H$_{12}$O$_4$) | | |
|---|---|---|
| | C | H |
| Calculated | 63.45 | 5.81 |
| Found | 63.47 | 5.76 |

Reference Example 6

Synthesis of methyl (S)-(+)-4-(oxiranylmethoxy)-benzoate

The same procedure of Reference Example 4 was repeated except that methyl 4-hydroxybenzoate was used in lieu of benzyl 4-hydroxybenzoate, and (S)-(+)-glycidyl toluenesulfonate was used in lieu of epibromohydrin to give the title compound (yield 90%).

Melting point: 34°–36° C. Specific rotation: $[\alpha]_D^{23}=+7.9°$ (c=1.0, CH$_2$Cl$_2$) NMR spectrum (CDCl$_3$) δ 2.79 (1H, dd, J=5.0, 2.6 Hz), 2.93(1H, dd, J=5.0, 4.3 Hz), 3.38(1H, dddd, J=5.8, 5.0, 4.3, 3.0, 2.6 Hz), 3.89(3 H, s), 3.99(1H, dd, J=11.2, 5.8 Hz), 4.30 (1H, dd, J=11.2, 3.0 Hz), 6.94(2H, d, J=8.9 Hz), 7.99(2H, d, J=8.9 Hz)

| Elementary analysis (for C$_{11}$H$_{12}$O$_4$) | | |
|---|---|---|
| | C | H |
| Calculated | 63.45 | 5.81 |
| Found | 63.20 | 5.79 |

Reference Example 7

Synthesis of 5-(chloromethyl)-3-(4-chlorophenyl)-2-oxooxazolidine

A toluene (10 ml) solution of 5.9 g of 4-chlorophenyl isocyanate and 3.3 ml of epichlorohydrin was added dropwise to a toluene (1 ml) solution of 0.2 g of lithium bromide and 0.42 g of tri-n-butylphosphine oxide at 100° C. The mixture was stirred at the same temperature for 3 hours. The reaction mixture was concentrated under reduced pressure. Ethanol was added to the obtained residue to collect the crystals by filtration. Thus, 8.9 g of the title compound was obtained (yield 93%).

Melting point: 119°–120° C. NMR spectrum (CDCl$_3$) δ3.75 (1H, dd, J=11.8, 6.5 Hz), 3.81(1H, dd, J=11.8, 4.1 Hz), 3.94(1H, dd, J=9.0, 5.8 Hz), 4.15(1H, dd, J=9.0, 8.9 Hz), 4.88(1H, m), 7.34 (2H, d, J=9.2 Hz), 7.50(2H, d, J=9.2 Hz)

| Elementary analysis (for C$_{10}$H$_9$NO$_2$Cl$_2$) | | | |
|---|---|---|---|
| | C | H | N |
| Calculated | 48.81 | 3.69 | 5.69 |
| Found | 48.56 | 3.71 | 5.53 |

Reference Example 8

Synthesis of (4S, 5S)-(−)-3-(4-methoxyphenyl)-4-methyl-2-oxooxazolidin-5-ylmethyl p-nitrobenzoate A xylene (6 ml) solution of 1.13 ml of 4-methoxyphenyl isocyanate and 2.06 g of (2S, 3S)-(−)-3-methylglycidyl p-nitrobenzoate was added dropwise to a xylene (1 ml) solution of 55 mg of lithium bromide and 110 mg of tri-n-butylphosphine oxide at 140° C. The mixture was stirred at the same temperature for 2 hours. The reaction mixture was concentrated under reduced pressure, and ethanol was added to the obtained residue to collect the crystals by filtration. Thus, 2.53 g of the title compound was obtained (yield 75%).

Melting point: 138°–140° C. Specific rotation: [α]$_D^{25}$=−55.39° (c=1.0, CHCl$_3$) NMR spectrum (CDCl$_3$) δ1.38 (3 H, d, J=6.2 Hz), 3.81(3 H, s), 4.23(1H, m), 4.4–4.75(3 H, m), 6.92 (2H, d, J=11.2 Hz), 7.27 (2H, d, J=11.2 HZ), 8.19 (2H, d, J=8.9 HZ), 8.28 (2H, d, J=8.9 Hz)

| Elementary analysis (for C$_{19}$H$_{18}$N$_2$O$_7$) | | | |
|---|---|---|---|
| | C | H | N |
| Calculated | 59.07 | 4.70 | 7.25 |
| Found | 59.38 | 4.73 | 7.42 |

Reference Example 9

Synthesis of (R)-(−)-3-(4-methoxyphenyl)-5-methyl-2-oxooxazolidin-5-ylmethyl p-nitrobenzoate The same procedure of Reference Example 8 was repeated except that (R)-(−)-2-methylglycidyl p-nitrobenzoate was used in lieu of (2S, 3S)-(−)-3-methylglycidyl p-nitrobenzoate to give the title compound (yield 92%).

Melting point:155°–157° C. Specific rotation: [α]$_D^{25}$= 7.28° (c=1.0, CHCl$_3$) NMR spectrum (CDCl$_3$) δ1.60 (3 H, s), 3.74(3 H, s), 3.94(1H, d, J=9.4 Hz), 4.10(1H, d, J=9.4 Hz), 4.49 (1H, d, J=11.8 Hz), 4.54 (1H, d, J=11.8 Hz), 6.97 (2H, d, J=9.2 Hz), 7.46 (2H, d, J=9.2 Hz), 8.12 (2H, d, J=8.9 Hz), 8.30 (2H, d, J=8.9 Hz)

| Elementary analysis (for C$_{19}$H$_{18}$N$_2$O$_7$) | | | |
|---|---|---|---|
| | C | H | N |
| Calculated | 59.07 | 4.70 | 7.25 |
| Found | 59.20 | 4.78 | 7.16 |

Reference Example 10

Synthesis of (S)-(+)-3-(4-methoxyphenyl)-5-methyl-2-oxooxazolidin-5-ylmethyl p-nitrobenzoate The same procedure of Reference Example 8 was repeated except that (S)-(+)-2-methylglycidyl p-nitrobenzoate was used in lieu of (2S, 3S)-(−)-3-methylglycidyl p-nitrobenzoate to give the title compound (yield 96% ).

Melting point: 156°–158° C. Specific rotation: [α]$_D^{25}$=+ 71.79° (c=1.0, CHCl$_3$) NMR spectrum (CDCl$_3$) δ1.60 (3H, s), 3.74(3H, s), 3.94(1H, d, J=9.4 Hz), 4.10(1H, d, J=9.4 Hz), 4.49 (1H, d, J=11.8 Hz), 4.54 (1H, d, J=11.8 Hz), 6.97 (2H, d, J=9.2 Hz), 7.46 (2H, d. J=9.2 Hz), 8.12 (2H, d, J=8.9 Hz), 8.30 (2H, d, J=8.9 Hz)

| Elementary analysis (for C$_{19}$H$_{18}$N$_2$O$_7$) | | | |
|---|---|---|---|
| | C | H | N |
| Calculated | 59.07 | 4.70 | 7.25 |
| Found | 59.28 | 4.69 | 7.22 |

Reference Example 11

Synthesis of (4S, 5S)-(−)-3-(4-methoxyphenyl)-4-methyl-2-oxooxazolidin-5-ylmethyl alcohol A 3.8 ml quantity of 8% sodium hydroxide aqueous solution was added to a methanol (20 ml) solution of 2.43 g of (4S, 5S)-(−)-3-(4-methoxyphenyl)-4-methyl-2-oxooxazolidin-5-ylmethyl p-nitrobenzoate obtained in Reference Example 8. The mixture was stirred at 50° C. for 20 minutes. The reaction mixture was concentrated under reduced pressure, and the obtained residue was extracted with ethyl acetate. The extract was washed with water, dried with magnesium sulfate and filtered. The filtrate was concentrated under reduced pressure, and the residue was subjected to silica gel column chromatography and purified by hexane-ethyl acetate gradient elution to give 1.04 g of the title compound (yield 70%).

Melting point: 99°–101° C. Specific rotation: [α]$_D^{25}$=− 21.19° (c=1.0, CHCl$_3$) NMR spectrum (CDCl$_3$) δ1.29 (3 H, d, J=5.9 Hz), 2.13 (1H, dd, J=7.3, 6.3 Hz), 3.75 (1H, ddd, J=12.5, 4.0, 3.6 Hz), 3.81 (3H, s), 3.98 (1H, ddd, J=12.5, 6.0, 3.0 Hz), 4.2–4.34 (2H, m), 6.92 (2H, d, J=9.2 Hz), 7.26 (2H, d, J=9.2 Hz)

Reference Example 12

Synthesis of (R)-(−)-3-(4-methoxyphenyl)-5-methyl-2-oxooxazolidin-5-ylmethyl alcohol The same procedure of Reference Example 11 was repeated except that (R)-(−)-3-(4-methoxyphenyl)-5-methyl-2-oxooxazolidin-5-ylmethyl p-nitrobenzoate obtained in Reference Example 9 was used in lieu of (4S, 5S)-(−)-3-(4-methoxyphenyl)-4-methyl-2-oxooxazolidin-5-ylmethyl p-nitrobenzoate to give the title compound (yield 90% ).

Melting point: 133°–134° C. Specific rotation: $[\alpha]_D^{25}=$ –24.89° (c=1.0, CHCl$_3$) NMR spectrum (CDCl$_3$) δ1.50 (3H, s), 2.39 (1H, dd, J=8.3, 5.6 Hz), 3.58 (1H, dd, J=12.2, 8.3 Hz), 3.63 (1H, d, J=8.6 Hz), 3.78 (1H, dd, J=12.2, 5.6 Hz), 3.80 (3H, s), 4.08 (1H, d, J=8.6 Hz), 6.89 (2H, d, J=8.9 Hz), 7.43 (2H, d, J=8.9 Hz)

Reference Example 13

Synthesis of (S)-(+)-3-(4-methoxyphenyl)-5-methyl-2-oxooxazolidin-5-ylmethyl alcohol The same procedure of Reference Example 11 was repeated except that (S)-(+)-3-(4-methoxyphenyl)-5-methyl-2-oxooxazolidin-5-ylmethyl p-nitrobenzoate obtained in Reference Example 10 was used in lieu of (4S, 5S)-(–)-3-(4-methoxyphenyl)-4-methyl-2-oxooxazolidin-5-ylmethyl p-nitrobenzoate to give the title compound (yield 95%).

Melting point: 131°–132° C. Specific rotation: $[\alpha]_D^{25}=$+ 21.39° (c=1.0, CHCl$_3$) NMR spectrum (CDCl$_3$) δ1.50 (3H, s), 2.39 (1H, dd, J=8.3, 5.6 Hz), 3.58 (1H, dd, J=12.2, 8.3 Hz), 3.63 (1H, d, J=8.6 Hz), 3.78 (1H, dd, J=12.2, 5.6 Hz), 3.80 (3H, s), 4.08 (1H, d, J=8.6 Hz), 6.89 (2H, d, J=8.9 Hz), 7.43 (2H, d, J=8.9 Hz)

Reference Example 14

Synthesis of 4-[(4S, 5S)-(–)-3-(4-methoxyphenyl)-4-methyl-2-oxooxazolidin-5-yl]methoxybenzonitrile To a suspension of 200 mg of 60% sodium hydride in anhydrous N,N-dimethylformamide (1 ml) was added dropwise an N,N-dimethylformamide (7 ml) solution of 0.98 g of (4S, 5S)-(–)-3-(4-methoxyphenyl)-4-methyl-2-oxooxazolidin-5-ylmethyl alcohol obtained in Reference Example 11 at room temperature in a stream of nitrogen, and the mixture was stirred at 50° C. for 25 minutes. A solution of 500 mg of p-fluorobenzonitrile in anhydrous N,N-dimethylformamide (2 ml) was added thereto at the same temperature and the mixture was stirred for 30 minutes. The reaction mixture was concentrated under reduced pressure and the obtained residue was extracted with ethyl acetate. The extract was washed with water, dried with magnesium sulfate and filtered. The filtrate was concentrated under reduced pressure. The residue was subjected to silica gel column chromatography and purified by hexane-ethyl acetate gradient elution to give 0.98 g of the title compound (yield 70%).

Melting point: 127°–128° C. Specific rotation: $[\alpha]_D^{25}=$ –74.70° (c=1.0, CHCl$_3$) NMR spectrum (CDCl$_3$) δ1.39 (3H, d, J=6.3 Hz), 3.82 (3H, s), 4.28 (2H, d, J=4.6 Hz), 4.35 (1H, dq, J=4.9, 6.3 Hz), 3.51 (1H, dt, J=4.9, 4.6 Hz), 6.94 (2H, d, J=8.9 Hz), 6.99 (2H, d, J=8.9 Hz), 7.30 (2H, d, J=8.9 Hz), 7.62 (2H, d, J=8.9 Hz)

| Elementary analysis (for C$_{19}$H$_{18}$N$_2$O$_4$) | | | |
| --- | --- | --- | --- |
|  | C | H | N |
| Calculated | 67.45 | 5.36 | 8.28 |
| Found | 67.39 | 5.41 | 8.27 |

Reference Example 15

Synthesis of 4-[(R)-(–)-3-(4-methoxyphenyl)-5-methyl-2-oxooxazolidin-5-yl]methoxybenzonitrile The same procedure of Reference Example 14 was repeated except that (R)-(–)-3-(4-methoxyphenyl)-5-methyl-2-oxooxazolidin-5-ylmethyl alcohol obtained in Reference Example 12 was used in lieu of (4S, 5S)-(–)-3-(4-methoxyphenyl)-4-methyl-2-oxooxazolidin-5-ylmethyl alcohol to give the title compound (yield 76%).

Melting point: 147°–149° C. Specific rotation: $[\alpha]_D^{25}=$ –83.56° (c=1.0, CHCl$_3$)

NMR spectrum (CDCl$_3$) δ1.68 (3H, s), 3.79 (1H, d, J=8.9 Hz), 3.80 (3H, s), 4.03 (1H, d, J=9.6 Hz), 4.12 (1H, d, J=8.9 Hz), 4.17 (1H, d, J=9.6 Hz), 6.92 (2H, d, J=9.2 Hz), 6.96 (2H, d, J=9.2 Hz), 7.45 (2H, d, J=9.2 Hz), 7.60 (2H, d, J=9.2 Hz)

| Elementary analysis (for C$_{19}$H$_{18}$N$_2$O$_4$) | | | |
| --- | --- | --- | --- |
|  | C | H | N |
| Calculated | 67.45 | 5.36 | 8.28 |
| Found | 67.62 | 5.38 | 8.30 |

Reference Example 16

Synthesis of 4-[(S)-(+)-3-(4-methoxyphenyl)-5-methyl-2-oxooxazolidin-5-yl]methoxybenzonitrile The same procedure of Reference Example 14 was repeated except that (S)-(+)-3-(4-methoxyphenyl)-5-methyl-2-oxooxazolidin-5-ylmethyl alcohol obtained in Reference Example 13 was used in lieu of (4S, 5S)-(–)-3-(4-methoxyphenyl)-4-methyl-2-oxooxazolidin-5-ylmethyl alcohol to give the title compound (yield 76%).

Melting point: 146°–147° C. Specific rotation: $[\alpha]_D^{25}=$+ 73.86° (c=1.0, CHCl$_3$) NMR spectrum (CDCl$_3$) δ1.68 (3H, s), 3.79 (1H, d, J=8.9 Hz), 3.80 (3H, s), 4.03 (1H, d, J=9.6 Hz), 4.12 (1H, d, J=8.9 Hz), 4.17 (1H, d, J=9.6 Hz), 6.92 (2H, d, J=9.2 Hz), 6.96 (2H, d, J=9.2 Hz), 7.45 (2H, d, J=9.2 Hz), 7.60 (2H, d, J=9.2 Hz)

| Elementary analysis (for C$_{19}$H$_{18}$N$_2$O$_4$) | | | |
| --- | --- | --- | --- |
|  | C | H | N |
| Calculated | 67.45 | 5.36 | 8.28 |
| Found | 67.63 | 5.40 | 8.27 |

Reference Example 17

Synthesis of 3-(4-chlorophenyl)-2-oxooxazolidin-4-ylmethyl alcohol

A 8.5 ml quantity of triethylamine was added dropwise to a dichloromethane (25 ml) solution of 2.5 g of 4-chlorophenyl isocyanate and 2.5 g of glycidol at 40° C., and the mixture was stirred at the same temperature for 20 hours. The reaction mixture was washed with 5% hydrochloric acid, dried with magnesium sulfate and filtered. The filtrate was concentrated under reduced pressure. The residue was subjected to silica gel column chromatography and purified by dichloromethane-ethanol gradient elution to give 5.30 g of the title compound as an oil (yield 69%).

NMR spectrum (CDCl$_3$) δ2.50 (1H, t), 3.60–3.80 (2H, m), 4.40–4.60 (3H, m), 7.30–7.50 (4 H, m)

Reference Example 18

Synthesis of 3-phenyl-2-oxooxazolidin-4-ylmethyl alcohol

The same procedure of Reference Example 17 was repeated except that phenyl isocyanate was used in lieu of 4-chlorophenyl isocyanate to give the title compound as an oil (yield 31%).

NMR spectrum (CDCl$_3$) δ2.15 (1H, t), 3.65–3.85 (2H, m), 4.45–4.65 (3H, m), 7.20–7.55 (5H, m)

Reference Example 19

Synthesis of 3-(4-chlorophenyl)-2-oxooxazolidin-4-ylmethyl methanesulfonate

Methanesulfonyl chloride (3.0 g) was added dropwise to a dichloromethane (50 ml) solution of 5.30 g of 3-(4-chlorophenyl)-2-oxooxazolidin-4-ylmethyl alcohol obtained in Reference Example 17 and 8.5 ml of triethylamine with ice-cooling, and the mixture was stirred at the same temperature for 2 hours. The reaction mixture was washed with water, dried with magnesium sulfate and filtered. The filtrate was concentrated under reduced pressure. The residue was subjected to silica gel column chromatography and purified by chloroform-ethanol gradient elution to give 6.50 g of the title compound (yield 91%).

Melting point 124°–126° C.

| Elementary analysis (for C$_{11}$H$_{12}$NO$_5$ClS) | | | |
|---|---|---|---|
| | C | H | N |
| Calculated | 43.21 | 3.96 | 4.58 |
| Found | 43.04 | 4.16 | 4.61 |

Reference Example 20

Synthesis of 3-phenyl-2-oxooxazolidin-4-ylmethyl methanesulfonate

The same procedure of Reference Example 19 was repeated except that 3-phenyl-2-oxooxazolidin-4-ylmethyl alcohol obtained in Reference Example 18 was used in lieu of 3-(4-chlorophenyl)-2-oxooxazolidin-4-ylmethyl alcohol to give the title compound as an oil (yield 89%).

NMR spectrum (CDCl$_3$) δ3.88 (3H, s), 4.2–4.45 (3H, m), 4.55–4.80 (2H, m), 7.20–7.50 (5H, m)

Reference Example 21

Synthesis of 4-[3-(2-pyridyl)-2-oxooxazolidin-5-yl]methoxyaniline

A 0.47 g quantity of 10% palladium carbon was added to a solution of 4.64 g of 4-[3-(2-pyridyl)-2-oxooxazolidin-5-yl]methoxynitrobenzene in 50 ml of 1,4-dioxane and 150 ml of N,N-dimethylformamide. The mixture was stirred at room temperature for 2.5 hours in a stream of hydrogen under 5 atmospheric pressure. The reaction mixture was filtered, and the filtrate was concentrated under reduced pressure. Methanol was added to the obtained residue to collect the crystals by filtration. Thus, 3.41 g of the title compound was obtained (yield 81%).

Melting point: 141°–143° C. NMR spectrum (DMSO-d$_6$) δ4.02 (1H, dd, J=10.2, 6.6 Hz), 4.08 (1H, dd, J=11.2, 5.3 Hz), 4.15 (1H, dd, J=11.2, 3.3 Hz), 4.29 (1H, dd, J=10.2, 9.2 Hz), 4.66 (2H, s), 5.00 (1H, m), 6.50 (2H, d, J=8.9 Hz), 6.67 (2H, d, J=8.9 Hz), 7.14 (1H, dd, J=7.3, 5.0 Hz), 7.85 (1H, ddd, J=8.6, 7.3, 1.0 Hz), 8.10 (1H, d, J=8.6 Hz), 8.37 (1H, dd, J=5.0, 1.0 Hz)

| Elementary analysis (for C$_{15}$H$_{15}$N$_3$O$_3$) | | | |
|---|---|---|---|
| | C | H | N |
| Calculated | 63.15 | 5.30 | 14.73 |
| Found | 63.05 | 5.35 | 14.65 |

Reference Example 22

Synthesis of 4-[3-(4-chlorophenyl)-2-oxooxazolidin-5-yl]methoxyaniline and 4-(3-phenyl-2-oxooxazolidin-5-yl)methoxyaniline The same procedure of Reference Example 21 was repeated except that 3.65 g of a mixture of 4-[3-(4-chlorophenyl)-2-oxooxazolidin-5-yl]methoxynitrobenzene and 4-(3-phenyl-2-oxooxazolidin-5-yl)methoxynitrobenzene was used in lieu of 4-[3-(2-pyridyl)-2-oxooxazolidin-5-yl]methoxynitrobenzene to give 2.89 g of a mixture the title compounds.

Example 1

Synthesis of 4-[3-(4-methoxyphenyl)-2-oxooxazolidin-5-yl]methoxybenzaldehyde

The same procedure of Reference Example 8 was repeated except that 4-(oxiranylmethoxy)-benzaldehyde obtained in Reference Example 3 was used in lieu of (2S, 3S)-(−)-3-methylglycidyl p-nitrobenzoate to give the title compound (compound 1) in a yield of 91%.

Melting point: 135°–137° C. NMR spectrum (CDCl$_3$) δ3.81 (3H, s), 4.03 (1H, dd, J=8.9, 5.9 Hz), 4.21 (1H, t, J=8.9 Hz), 4.29 (1H, dd, J=10.2, 4.3 Hz), 4.33 (1H, dd, J=10.2, 4.6 Hz), 5.01 (1H, m), 6.93 (2H, d, J=9.2 Hz), 7.03 (2H, d, J=8.8 Hz), 7.46 (2H, d, J=9.2 Hz), 7.86 (2H, d, J=8.8 Hz), 9.91 (1H, s)

| Elementary analysis (for C$_{18}$H$_{17}$NO$_5$) | | | |
|---|---|---|---|
| | C | H | N |
| Calculated | 66.05 | 5.23 | 4.28 |
| Found | 66.23 | 5.36 | 4.40 |

Example 2

Using proper starting materials, compounds 2 to 34 shown in Table 1, compounds 35 to 39 shown in Table 2, compounds 40 to 43 shown in Table 3 and compounds 45 to 48 shown in Table 4 were synthesized in the same manner as in Example 1.

Example 3

Synthesis of methyl 4-[3-(4-nitrophenyl)-2-oxooxazolidin-5-yl]methoxybenzoate

A xylene (15 ml) solution of 5.4 g of 4-nitrophenyl isocyanate and 6.9 g of methyl 4-(oxiranylmethoxy)-benzoate was added dropwise to a xylene (2 ml) solution of 170 mg of lithium bromide and 360 mg of tri-n-butylphosphine oxide at 140° C. and the mixture was stirred at the same temperature for 2 hours, and the reaction mixture was concentrated under reduced pressure. Ethanol was added to the obtained residue to collect the crystals by filtration. Thus, 11.0 g of the title compound (compound 50) was obtained in a yield of 90%.

Melting point: 200°–201° C. NMR spectrum (DMSO-$d_6$) $\delta$3.82 (3H, s), 4.05 (1H, dd, J=9.2, 6.1 Hz), 4.34 (1H, dd, J=9.2, 9.2 Hz), 4.38 (1H, dd, J=11.2, 6.6 Hz), 4.44 (1H, dd, J=11.2, 3.3 Hz), 5.17 (1H, m), 7.07 (2H, d, J=8.9 Hz), 7.85 (2H, d, J=9.3 Hz), 7.92 (2H, d, J=8.9 Hz), 8.31 (2H, d, J=9.3 Hz)

| Elementary analysis (for $C_{18}H_{15}N_2O_7$) | | | |
|---|---|---|---|
| | C | H | N |
| Calculated | 58.07 | 4.33 | 7.52 |
| Found | 58.03 | 4.30 | 7.38 |

Example 4

Synthesis of methyl 4-[3-(4-chlorophenyl)-2-oxooxazolidin-5-yl]methoxybenzoate

A 1.52 g quantity of methyl 4-hydroxy-benzoate was added to a suspension of 0.42 g of 60% sodium hydride in anhydrous N,N-dimethylformamide (15 ml) with ice-cooling in a stream of nitrogen. To the mixture was added dropwise an anhydrous N,N-dimethylformamide (15 ml) solution of 2.46 g of 5-(chloromethyl)-3-(4-chlorophenyl)-2-oxooxazolidine obtained in Reference Example 7 at the same temperature, and the mixture was stirred at 40° C. for 48 hours. The reaction mixture was concentrated under reduced pressure, and the obtained residue was extracted with ethyl acetate. The extract was washed with water, dried with magnesium sulfate and filtered. The filtrate was then concentrated under reduced pressure. The residue was subjected to silica gel column chromatography and purified by hexane-ethyl acetate gradient elution to give 1.75 g of the title compound (compound 51) in a yield of 48%.

Melting point: 146°–148° C. NMR spectrum (CDCl$_3$) $\delta$3.89 (3H, s), 4.05 (1H, dd, J=8.9, 5.9 Hz), 4.20 (1H, dd, J=8.9, 8.9 Hz), 4.28 (1H, dd, J=10.2, 4.3 Hz), 4.31 (1H, dd, J=10.2, 4.6 Hz), 5.02 (1H, dddd, J=8.9, 5.9, 4.6, 4.3 Hz), 6.92 (2H, d, J=8.9 Hz), 7.36 (2H, d, J=8.9 Hz), 7.53 (2H, d, J=8.9 Hz), 8.01 (2H, d, J=8.9 Hz)

| Elementary analysis (for $C_{18}H_{16}NO_5Cl$) | | | |
|---|---|---|---|
| | C | H | N |
| Calculated | 59.76 | 4.46 | 3.87 |
| Found | 59.88 | 4.39 | 3.88 |

Example 5

Using proper starting materials, compounds 52 to 80 and 116 shown in Table 5, compound 117 shown in Table 6, compounds 119 to 128 shown in Table 7, compounds 136 to 143 shown in Table 8, compounds 153 to 160 shown in Table 9 and compounds 169 and 170 shown in Table 10 were synthesized in the same manner as in Example 3.

Example 6

Synthesis of methyl (R)-(−)-4-[3-(4-acetylphenyl)-2-oxooxazolidin-5-yl]methoxybenzoate The same procedure of Example 4 was repeated except that (R)-(−)-4-[3-(4-acetylphenyl)-2-oxooxazolidin-5-yl] methyl methanesulfonate was used in lieu of 5-(chloromethyl)-3-(4-chlorophenyl)-2-oxooxazolidine to give the title compound (compound 144) in a yield of 82%.

Melting point: 130°–132° C. Specific rotation: $[\alpha]_D^{25}$32 −107.6° (c=1.0, CH$_2$Cl$_2$) NMR spectrum (CDCl$_3$) $\delta$2.60 (3H, s), 3.89 (3H, s), 4.13 (1H, dd, J=8.9, 5.9 Hz), 4.25–4.37 (3H, m), 5.05 (1H, m), 6.92 (2H, d, J=8.9 Hz), 7.69 (2H, d, J=8.9 Hz), 8.00 (2H, d, J=8.9 Hz), 8.01 (2H, d, J=8.9 Hz)

| Elementary analysis (for $C_{20}H_{19}NO_6$) | | | |
|---|---|---|---|
| | C | H | N |
| Calculated | 65.03 | 5.18 | 3.79 |
| Found | 65.00 | 5.24 | 3.79 |

Example 7

Synthesis of 4-[3-(4-nitrophenyl)-2-oxooxazolidin-5-yl] methoxybenzoic acid

A solution of 2.0 g of methyl 4-[3-(4-nitrophenyl)-2-oxooxazolidin-5-yl]methoxybenzoate (compound 50) obtained in Example 3 in 18 ml of acetic acid and 6 ml of concentrated hydrochloric acid was refluxed with heating for 12 hours. After ice-cooling the reaction solution, ether was added thereto and the crystals formed were collected by filtration. Thus, 1.64 g of the title compound (compound 81) was obtained (yield 85%).

Melting point: 236°–238° C. NMR spectrum (DMSO-$d_6$) $\delta$4.04 (1H, dd, J=9.2, 6.0 Hz), 4.34 (1H, dd, J=9.2, 9.2 Hz), 4.38 (1H, dd, J=11.2, 6.6 Hz), 4.44 (1H, dd, J=11.2, 3.3 Hz), 5.17 (1H, m), 7.04 (2H, d, J=8.9 Hz), 7.85 (2H, d, J=9.3 Hz), 7.92 (2H, d, J=8.9 Hz), 8.31 (2H, d, J=9.3 Hz), 12.68 (1H, s)

| Elementary analysis ($C_{17}H_{14}N_2O_7$) | | | |
|---|---|---|---|
| | C | H | N |
| Calculated | 56.99 | 3.94 | 7.82 |
| Found | 57.13 | 4.16 | 7.82 |

Example 8

Using proper starting materials, compounds 82 to 111 shown in Table 5, compound 118 shown in Table 6, compounds 129 to 133 shown in Table 7, compounds 145 to 152 shown in Table 8 and compounds 161 to 168 shown in Table 9 were synthesized in the same manner as in Example 7.

Example 9

Synthesis of methyl 4-[3-(4-aminophenyl)-2-oxooxazolidin-5-yl]methoxybenzoate

A 6.0 g quantity of zinc powder was added to an acetic acid (60 ml) solution of 3.0 g of methyl 4-[3-(4-nitrophenyl)-2-oxooxazolidin-5-yl]methoxybenzoate (compound 50) obtained in Example 3 at 60° C., and the mixture was stirred at the same temperature for 3 hours. The reaction mixture was filtered and the filtrate was concentrated under reduced pressure. Ethanol was added to the obtained residue to collect the crystals by filtration. Thus, 3.0 g of the title compound (compound 112) was obtained in a quantitative yield.

Melting point: 139°–142° C. NMR spectrum (DMSO-$d_6$) δ3.81 (1H, dd, J=8.9, 6.3 Hz), 3.82 (3H, s), 4.12 (1H, dd, J=9.2, 8.9 Hz), 4.30 (1H, dd, J=11.2, 5.3 Hz), 5.0 (1H, m), 6.58 (2H, d, J=8.6 Hz), 7.09 (2H, d, J=8.9 Hz), 7.18 (2H, d, J=8.6 Hz), 7.93 (2H, d, J=8.9 Hz) MASS spectrum (EI) m/z 342 ($M^+$)

Example 10

Synthesis of methyl 4-[3-(4-acetamidophenyl)-2-oxooxazolidin-5-yl]methoxybenzoate A 1.2 ml quantity of anhydrous acetic acid was added dropwise to an acetic acid (60 ml) solution of 3.0 g of methyl 4-[3-(4-aminophenyl)-2-oxooxazolidin-5-yl]methoxybenzoate obtained in Example 9 at room temperature, and the mixture was stirred at the same temperature for 1 hour. The crystals were collected by filtration and washed with ethanol to give 3.05 g of the title compound (compound 113) in a yield of 99%.

Melting point: 188°–190° C. NMR spectrum (DMSO-$d_6$) δ2.03 (3H, s), 3.82 (3H, s), 3.91 (1H, dd, J=8.9, 6.3 Hz), 4.21 (1H, dd, J=9.1, 8.9 Hz), 4.33 (1H, dd, J=11.0, 5.3 Hz), 4.39 (1H, dd, J=11.0, 3.3 Hz), 5.07 (1H, m), 7.08 (2H, d, J=8.9 Hz), 7.50 (2H, d, J=9.2 Hz) 7.60 (2H, d, J=9.2 Hz), 7.93 (2H, d, J=8.9 Hz), 9.95 (1H, s)

| Elementary analysis (for $C_{20}H_{20}N_2O_6 \cdot \frac{1}{4}H_2O$) | | | |
|---|---|---|---|
| | C | H | N |
| Calculated | 61.77 | 5.31 | 7.20 |
| Found | 61.55 | 5.20 | 7.07 |

Example 11

Synthesis of 4-[3-(4-aminophenyl)-2-oxooxazolidin-5-yl]methoxybenzoic acid hydrochloride The same procedure of Example 7 was repeated except that methyl 4-[3-(4-aminophenyl)-2-oxooxazolidin-5-yl]methoxybenzoate (compound 112) obtained in Example 9 was used in lieu of methyl 4-[3-(4-nitrophenyl)-2-oxooxazolidin-5-yl]methoxybenzoate to give the title compound (compound 114) in a yield of 64%.

Melting point: 248°–252° C. (decomposition) NMR spectrum (DMSO-$d_6$) δ3.91 (1H, dd, J=8.9, 6.3 Hz), 4.21 (1H, dd, J=9.2, 8.9 Hz), 4.33 (1H, dd, J=10.9, 5.3 Hz), 4.38 (1H, dd, J=10.9, 3.3 Hz), 5.10 (1H, m), 7.05 (2H, d, J=8.9 Hz), 7.50 (2H, d, J=8.9 Hz), 7.69 (2H, d, J=8.9 Hz), 7.90 (2H, d, J=8.9 Hz)

| Elementary analysis (for $C_{17}H_{16}N_2O_5 \cdot HCl$) | | | |
|---|---|---|---|
| | C | H | N |
| Calculated | 55.96 | 4.70 | 7.68 |
| Found | 55.65 | 4.64 | 7.69 |

Example 12

Synthesis of 4-[3-(4-acetamidophenyl)-2-oxooxazolidin-5-yl]methoxybenzoic acid

The same procedure of Example 10 was repeated except that 4-[3-(4-aminophenyl)-2-oxooxazolidin-5-yl]methoxybenzoic acid (compound 114) obtained Example 11 was used in lieu of methyl 4-[3-(4-aminophenyl)-2-oxooxazolidin-5-yl]methoxybenzoate to give the title compound (compound 115) in a yield of 88%.

Melting point: 288°–291° C. NMR spectrum (DMSO-$d_6$) δ3.91 (1H, dd, J=8.9, 6.3 Hz), 4.21 (1H, dd, J=9.2, 8.9 Hz), 4.33 (1H, dd, J=10.9, 5.3 Hz), 4.38 (1H, dd, J=10.9, 3.3 Hz), 5.07 (1H, m), 7.04 (2H, d, J=8.9 Hz), 7.51 (2H, d, J=8.9 Hz), 7.60 (2H, d, J=8.9 Hz), 7.90 (2H, d, J=8.9 Hz), 9.94 (1H, s), 12.64 (1H, s)

| Elementary analysis (for $C_{19}H_{18}N_2O_6$) | | | |
|---|---|---|---|
| | C | H | N |
| Calculated | 61.62 | 4.90 | 7.56 |
| Found | 61.30 | 4.93 | 7.54 |

Example 13

Synthesis of 4-(3-benzoyl-2-oxooxazolidin-5-yl)methoxybenzoic acid.

A 1.0 g quantity of 10% palladium carbon was added to a solution of 3.8 g of benzyl 4-(3-benzoyl-2-oxooxazolidin-5-yl)methoxybenzoate (compound 120) obtained in Example 5 in 50 ml of acetic acid and 25 ml of N,N-dimethylformamide. The mixture was stirred at 60° C. for 5 hours in a stream of hydrogen. The reaction mixture was filtered and the filtrate was concentrated under reduced pressure. Ethanol was added to the obtained residue to collect the crystals by filtration. Thus, 235 mg of the title compound (compound 134) was obtained (yield 8%).

Melting point: 219°–221° C. NMR spectrum (DMSO-$d_6$) δ3.96 (1H, dd, J=10.6, 5.9 Hz), 4.24 (1H, dd, J=10.6, 8.9 Hz), 4.42 (2H, m), 5.12 (1H, m), 7.08 (2H, d, J=8.9 Hz), 7.4–7.7 (4 H, m), 7.85–7.95 (3H, m)

| Elementary analysis (for $C_{18}H_{15}NO_6$) | | | |
|---|---|---|---|
| | C | H | N |
| Calculated | 63.34 | 4.43 | 4.10 |
| Found | 63.24 | 4.37 | 4.07 |

Example 14

Synthesis of 4-[3-(4-methylbenzenesulfonyl)-2-oxooxazolidin-5-yl]methoxybenzoic acid The same procedure of Example 13 was repeated except that benzyl 4-[3-(4-methylbenzenesulfonyl)-2-oxooxazolidin-5-yl]methoxybenzoate (compound 123) obtained in Example 5 was used in lieu of benzyl 4-(3-benzoyl-2-oxooxazolidin-5-yl)methoxybenzoate to give the title compound (compound 135) in a yield of 62%.

Melting point: 252°–254° C. NMR spectrum (DMSO-$d_6$) δ2.46 (3H, s), 3.99 (1H, dd, J=9.2, 5.6 Hz), 4.21–4.33 (3H, m), 5.07 (1H, m), 6.80 (2H, d, J=8.9 Hz), 7.52 (2H, d, J=8.2 Hz), 7.86 (2H, d, J=8.9 Hz), 7.90 (2H, d, J=8.2 Hz)

Elementary analysis (for C$_{18}$H$_{17}$NO$_7$S)

|  | C | H | N |
|---|---|---|---|
| Calculated | 55.24 | 4.38 | 3.58 |
| Found | 55.26 | 4.36 | 3.60 |

Example 15

Synthesis of 4-(3-phenyl-2-oxazolidinethion-5-yl)methoxybenzoic acid

A 8.7 ml quantity of aqueous solution of 0.5N potassium hydroxide was added to 75% ethanol (80 ml) solution of 750 mg of methyl 4-(3-phenyl-2-thiooxooxazolidin-5-yl)methoxybenzoate (compound 169) obtained in Example 5, and the mixture was stirred at room temperature for 5 days. The reaction mixture was concentrated under reduced pressure, and a dilute hydrochloric acid was added to the obtained residue and the crystals were collected by filtration. Thus, 235 mg of the title compound (compound 171) was obtained (yield 33%).

Melting point: 214°–215° C. NMR spectrum (DMSO-d$_6$) δ3.45 (1H, dd, J=11.2, 8.6 Hz), 3.66 (1H, dd, J=11.2, 6.6 Hz), 4.36 (1H, dd, J=10.9, 5.9 Hz), 4.44 (1H, dd, J=10.9, 3.4 Hz), 5.08 (1H, m), 6.88 (2H, d, J=7.3 Hz), 6.95–7.4 (5H, m), 7.93 (2H, d, J=8.9 Hz), 12.69 (1H, s)

Elementary analysis (for C$_{17}$H$_{15}$NO$_4$S)

|  | C | H | N |
|---|---|---|---|
| Calculated | 61.99 | 4.59 | 4.25 |
| Found | 61.99 | 4.60 | 4.09 |

Example 16

Synthesis of 4-[(4S, 5S)-(–)-3-(4-methoxyphenyl)-4-methyl-2-oxooxazolidin-5-yl]methoxybenzaldehyde A 1.8 g quantity of Raney nickel was added to a solution of 0.88 g of 4-[(4S, 5S)-(–)-3-(4-methoxyphenyl)- 4-methyl-2-oxooxazolidin-5-yl]methoxybenzonitrile obtained in Reference Example 14 in 25 ml of an 80% aqueous solution of formic acid. The mixture was refluxed with heating for 1.5 hours. The reaction mixture was concentrated under reduced pressure, and the obtained residue was extracted with ethyl acetate. The extract was washed with an aqueous solution of sodium bicarbonate, dried with magnesium sulfate and filtered. The filtrate was concentrated under reduced pressure. The residue was subjected to silica gel column chromatography and purified by hexane-ethyl acetate gradient elution to give 0.71 g of the title compound (compound 172) in a yield of 80%.

Melting point: 115°–116° C. Specific rotation: [α]$_D^{25}$=–68.99° (c=1.0, CHCl$_3$) NMR spectrum (CDCl$_3$) δ1.39 (3H, d, J=6.0 Hz), 3.82 (3H, s), 4.31 (2H, d, J=4.6 Hz), 4.37 (1H, dq, J=4.9, 6.3 Hz), 3.52 (1H, dt, J=4.9, 4.6 Hz), 6.94 (2H, d, J=8.9 Hz), 7.04 (2H, d, J=8.9 Hz), 7.31 (2H, d, J=8.9 Hz), 7.87 (2H, d, J=8.9 Hz), 9.92 (1H, s)

Elementary analysis (for C$_{19}$H$_{19}$NO$_5$)

|  | C | H | N |
|---|---|---|---|
| Calculated | 66.85 | 5.61 | 4.10 |
| Found | 67.02 | 5.82 | 4.30 |

Example 17

Synthesis of 4-[(R)-(–)-3-(4-methoxyphenyl)-5-methyl-2-oxooxazolidin-5-yl]methoxybenzaldehyde The same procedure of Example 16 was repeated except that 4-[(R)-(–)-3-(4-methoxyphenyl)-5-methyl-2-oxooxazolidin-5-yl]methoxybenzonitrile obtained in Reference Example 15 was used in lieu of 4-[(4S, 5S)-(–)-3-(4-methoxyphenyl)-4-methyl-2-oxooxazolidin-5-yl]methoxybenzonitrile to give the title compound (compound 44) as an oil (yield 85%).

Specific rotation: [α]$_D^{25}$=–75.79° (c=1.0, CHCl$_3$) NMR spectrum (CDCl$_3$) δ1.69 (3H, s), 3.80 (1H, d, J=8.9 Hz), 3.81 (3H, s), 4.07 (1H, d, J=9.6 Hz), 4.13 (1H, d, J=8.9 Hz), 4.21 (1H, d, J=9.6 Hz), 6.92 (2H, d, J=9.2 Hz), 7.01 (2H, d, J=8.9 Hz), 7.46 (2H, d, J=9.2 Hz), 7.85 (2H, d, J=8.9 Hz), 9.90 (1H, s)

Elementary analysis (for C$_{19}$H$_{19}$N$_2$O$_5$·⅓H$_2$O)

|  | C | H | N |
|---|---|---|---|
| Calculated | 66.16 | 5.67 | 4.06 |
| Found | 66.32 | 5.66 | 4.09 |

Example 18

Synthesis of 4-[(S)-(+)-3-(4-methoxyphenyl)-5-methyl-2-oxooxazolidin-5-yl]methoxybenzaldehyde The same procedure of Example 16 was repeated except that 4-[(S)-(+)-3-(4-methoxyphenyl)-5-methyl-2-oxooxazolidin-5-yl]methoxybenzonitrile obtained in Reference Example 16 was used in lieu of 4-[(4S, 5S)-(–)-3-(4-methoxyphenyl)-4-methyl-2-oxooxazolidin-5-yl]methoxybenzonitrile to give the title compound (compound 49) as an oil (yield 85%).

Specific rotation: [α]$_D^{25}$=+72.39° (c=1.0, CHCl$_3$) NMR spectrum (CDCl$_3$) δ1.69 (3H, s), 3.80 (1H, d, J=8.9 Hz), 3.81 (3H, s), 4.07 (1H, d, J=9.6 Hz), 4.13 (1H, d, J=8.9 Hz), 4.21 (1H, d, J=9.6 Hz), 6.92 (2H, d, J=9.2 Hz), 7.01 (2H, d, J=8.9 Hz), 7.46 (2H, d, J=9.2 Hz), 7.85 (2H, d, J=8.9 Hz), 9.90 (1H, s)

Elementary analysis (for C$_{19}$H$_{19}$N$_2$O$_5$·⅓H$_2$O)

|  | C | H | N |
|---|---|---|---|
| Calculated | 66.16 | 5.67 | 4.06 |
| Found | 66.34 | 5.77 | 4.04 |

Example 19

Synthesis of 4-[3-(4-formylphenyl)-2-oxooxazolidin-5-yl]methoxybenzaldehyde

The same procedure of Example 16 was repeated except that 4-[3-(4-cyanophenyl)-2-oxooxazolidin-5-yl]methoxybenzaldehyde (compound 34) obtained in Example 2 was used in lieu of 4-[(4S, 5S)-(–)-3-(4-methoxyphenyl)-4-methyl-2-oxooxazolidin-5-yl]methoxybenzonitrile to give the title compound (compound 173) in a yield of 89%.

Melting point: 130°–132° C. NMR spectrum (CDCl$_3$) δ4.15 (1H, dd, J=11.9, 5.9 Hz), 4.27–4.41 (3H, m), 5.04–5.14 (1H, m), 7.02 (2H, d, J=8.9 Hz), 7.78 (2H, d, J=8.9 Hz), 7.86 (2H, d, J=8.9 Hz), 7.93 (2H, d, J=8.9 Hz), 9.91 (1H, s), 9.97 (1H, s)

| Elementary analysis (for C$_{18}$H$_{15}$NO$_5$) | | | |
|---|---|---|---|
| | C | H | N |
| Calculated | 66.46 | 4.65 | 4.31 |
| Found | 66.39 | 4.70 | 4.60 |

Example 20

Synthesis of 4-[3-(4-chlorophenyl)-2-oxooxazolidin-5-yl] methoxybenzyl alcohol

A 114 mg quantity of sodium borohydride was added to a methanol (30 ml) solution of 1.00 g of 4-[3-(4-chlorophenyl)-2-oxooxazolidin-5-yl]-methoxybenzaldehyde (compound 7) obtained in Example 2, and the mixture was stirred at 60° C. for 5 minutes. The reaction mixture was concentrated under reduced pressure. To the obtained residue was added a 5% hydrochloric acid, and the mixture was extracted with ethyl acetate. The extract was washed with an aqueous solution of sodium chloride, dried with magnesium sulfate and filtered. The filtrate was concentrated under reduced pressure. The obtained residue was recrystallized from ethanol to give 862 mg of the title compound (compound 174) in a yield of 86%.

Melting point: 149°–150° C. NMR spectrum (CDCl$_3$) δ4.05 (1H, dd, J=8.9, 5.9 Hz), 4.18 (1H, t, J=8.9 Hz), 4.23 (2H, d, J=4.6 Hz), 4.63 (2H, s), 4.95–5.03 (1H, m), 6.89 (2H, d, J=8.9 Hz), 7.30 (2H, d, J=8.9 Hz), 7.35 (2H, d, J=9.2 Hz), 7.53 (2H, d, J=9.2 Hz)

| Elementary analysis (for C$_{17}$H$_{16}$NO$_4$Cl) | | | |
|---|---|---|---|
| | C | H | N |
| Calculated | 61.18 | 4.83 | 4.20 |
| Found | 61.40 | 4.74 | 4.27 |

Example 21

Synthesis of 4-[3-(4-tolyl)-2-oxooxazolidin-5-yl]methoxybenzyl alcohol

The same procedure of Example 20 was repeated except that 4-[3-(4-tolyl)-2-oxooxazolidin-5-yl]methoxybenzaldehyde (compound 20) obtained in Example 2 was used in lieu of 4-[3-(4-chlorophenyl)-2-oxooxazolidin-5-yl]methoxybenzaldehyde to give the title compound (compound 175) in a yield of 63%.

Melting point: 163°–165° C. NMR spectrum (CDCl$_3$) δ2.34 (3H, s), 4.04 (1H, dd, J=8.9, 5.9 Hz), 4.18 (1H, dd, J=8.9, 8.6 Hz), 4.22 (2H, d, J=4.6 Hz), 4.63 (2H, s), 4.92–5.04 (1H, m), 6.89 (2H, d, J=8.6 Hz), 7.19 (2H, d, J=8.6 Hz), 7.30 (2H, d, J=8.6 Hz), 7.44 (2H, d, J=8.6 Hz )

| Elementary analysis (for C$_{18}$H$_{19}$NO$_4$) | | | |
|---|---|---|---|
| | C | H | N |
| Calculated | 69.00 | 6.11 | 4.47 |
| Found | 69.06 | 6.24 | 4.40 |

Example 22

Synthesis of methyl 4-[3-(4-chlorophenyl)-2-oxooxazolidin-4-yl]methoxybenzoate

In 20 ml of N,N-dimethylformamide was dissolved 1.50 g of 3-(4-chlorophenyl)-2-oxooxazolidin-4-ylmethyl methanesulfonate and 0.80 g of methyl 4-hydroxybenzoate. To the solution was added 0.80 g of anhydrous potassium carbonate, and the mixture was stirred at 60° C. for 12 hours. The reaction mixture was concentrated under reduced pressure and water was added thereto. The obtained residue was recrystallized from methanol to give 1.60 g of the title compound (compound 176) in a yield of 90%.

Melting point: 135°–136° C.

| Elementary analysis (for C$_{18}$H$_{16}$NO$_5$Cl) | | | |
|---|---|---|---|
| | C | H | N |
| Calculated | 59.76 | 4.46 | 3.87 |
| Found | 59.67 | 4.56 | 3.96 |

Example 23

Synthesis of methyl 4-(3-phenyl-2-oxooxazolidin-4-yl)methoxybenzoate

The same procedure of Example 22 was repeated except that 3-phenyl-2-oxooxazolidin-4-ylmethyl methanesulfonate obtained in Reference Example 20 was used in lieu of 3-(4-chlorophenyl)-2-oxooxazolidin-4-ylmethyl methanesulfonate to give the title compound (compound 177) in a yield of 60%.

Melting point: 158°–159° C.

| Elementary analysis (for C$_{18}$H$_{17}$NO$_5$) | | | |
|---|---|---|---|
| | C | H | N |
| Calculated | 66.05 | 5.23 | 4.28 |
| Found | 66.09 | 5.21 | 4.34 |

Example 24

Synthesis of 4-[3-(4-chlorophenyl)-2-oxooxazolidin-4-yl] methoxybenzaldehyde

The same procedure of Example 22 was repeated except that 4-hydroxybenzaldehyde was used in lieu of methyl 4-hydroxybenzoate to give the title compound (compound 178) in a yield of 92%.

Melting point: 120°–122° C.

Elementary analysis (for $C_{17}H_{14}NO_4Cl$)

|  | C | H | N |
|---|---|---|---|
| Calculated | 61.55 | 4.25 | 4.22 |
| Found | 61.48 | 4.70 | 4.22 |

Example 25

Synthesis of 4-[3-(4-chlorophenyl)-2-oxooxazolidin-4-yl]methoxybenzoic acid

A solution of 1.30 g of methyl 4-[3-(4-chlorophenyl)-2-oxooxazolidin-4-yl]methoxybenzoate (compound 176) obtained in Example 22 in 18 ml of acetic acid and 10 ml of concentrated hydrochloric acid was refluxed with heating for 24 hours. The reaction mixture was concentrated under reduced pressure and the obtained residue was recrystallized from acetic acid-water to give 0.80 g of the title compound (compound 179) in a yield of 64%.

Melting point: 219°–221° C.

Elementary analysis (for $C_{17}H_{14}NO_5Cl$)

|  | C | H | N |
|---|---|---|---|
| Calculated | 66.05 | 5.23 | 4.28 |
| Found | 66.09 | 5.21 | 4.34 |

Example 26

Synthesis of 4-(3-phenyl-2-oxooxazolidin-4-yl)methoxybenzoic acid

The same procedure of Example 25 was repeated except that methyl 4-(3-phenyl-2-oxooxazolidin-4-yl)methoxybenzoate (compound 177) obtained in Example 23 was used in lieu of methyl 4-[3-(4-chlorophenyl)-2-oxooxazolidin-4-yl]methoxybenzoate to give the title compound (compound 180) in a yield of 61%.

Melting point: 255°–257° C.

Elementary analysis (for $C_{17}H_{15}NO_5 \cdot \frac{1}{3} H_2O$)

|  | C | H | N |
|---|---|---|---|
| Calculated | 64.43 | 4.90 | 4.42 |
| Found | 64.57 | 4.81 | 4.39 |

Example 27

Synthesis of 4-(3-phenyl-2-oxooxazolidin-5-yl)methoxycinnamic acid

In 1 ml of pyridine was dissolved 250 mg of 4-(3-phenyl-2-oxooxazolidin-5-yl)methoxybenzaldehyde (compound 19) obtained in Example 2 and 131 mg of malonic acid. Piperidine (0.05 ml) was added to the solution, and the mixture was stirred at 100° C. for 3 hours. To the mixture was added 10% sulfic acid, and the obtained residue was washed with methanol to give 240 mg of the title compound (compound 181) in a yield of 84%.

Melting point: 239°–240° C. NMR spectrum (DMSO-$d_6$) δ3.93 (1H, dd, J=9.2, 6.3 Hz), 4.26 (1H, dd, J=9.2, 8.9 Hz), 4.30 (1H, dd, J=11.2, 5.6 Hz), 4.36 (1H, dd, J=11.2, 3.6 Hz), 5.03–5.12 (1H, m), 6.39 (1H, d, J=15.8 Hz), 7.00 (2H, d, J=8.9 Hz), 7.14 (1H, t, J=7.3 Hz), 7.41 (2H, dd, J=8.2, 7.3 Hz), 7.52–7.67 (5H, m)

Elementary analysis (for $C_{19}H_{17}NO_5$)

|  | C | H | N |
|---|---|---|---|
| Calculated | 67.25 | 5.05 | 4.13 |
| Found | 67.59 | 4.95 | 4.28 |

Example 28

Using proper starting materials, compounds 182 to 184 shown in Table 14 were synthesized in the same manner as in Example 27.

Example 29

Synthesis of methyl 4-(3-phenyl-2-oxooxazolidin-5-yl)methoxycinnamate

In 20 ml of methanol was dissolved 200 mg of 4-(3-phenyl-2-oxooxazolidin-5-yl)methoxycinnamic acid (compound 181) obtained in Example 27. Concentrated sulfic acid (0.05 ml) was added to the solution, and the mixture was refluxed with heating for 16 hours. The reaction mixture was concentrated under reduced pressure and the obtained residue was washed with water and methanol to give 195 mg of the title compound (compound 185) in a yield of 94%.

Melting point: 179°–181° C. NMR spectrum (CDCl$_3$) δ3.79 (3H, s), 4.06 (1H, dd, J=8.9, 5.9 Hz), 4.22 (1H, dd, J=8.9, 7.6 Hz), 4.25 (2H, d, J=4.6 Hz), 4.95–5.04 (1 H, m), 6.32 (1H, d, J=15.8 Hz), 6.91 (2H, d, J=8.9 Hz), 7.16 (1H, dd, J=8.2, 7.3 Hz), 7.36–7.67 (7H, m)

Elementary analysis (for $C_{20}H_{19}NO_5$)

|  | C | H | N |
|---|---|---|---|
| Calculated | 67.98 | 5.42 | 3.96 |
| Found | 67.51 | 5.66 | 3.97 |

Example 30

Using proper starting materials, compounds 186 to 188 shown in Table 14 were synthesized in the same manner as in Example 29.

Example 31

Synthesis of methyl 3-[4-(3-phenyl-2-oxooxazolidin-5-yl)methoxyphenyl]propionate A 200 mg quantity of 10% palladium carbon was added to a tetrahydrofuran (50 ml) solution of 1.75 g of methyl 4-(3-phenyl-2-oxooxazolidin-5-yl)methoxycinnamate (compound 185) obtained in Example 29. The mixture was stirred at room temperature for 2.5 hours in a stream of hydrogen at 3 atmospheric pressure. The reaction mixture was filtered, and the filtrate was concentrated under reduced pressure and washed with methanol to give 1.59 g of the title compound (compound 189) in a yield of 88%.

Melting point: 138°–139° C. NMR spectrum (CDCl$_3$) δ2.59 (2H, t, J=7.6 Hz), 2.90 (2H, t, J=7.6 Hz), 3.66 (3H, s), 4.06 (1H, dd, J=8.9, 5.9 Hz), 4.15–4.24 (3H, m), 4.93–5.02 (1H, m), 6.83 (2H, d, J=8.6 Hz), 7.12 (2H, d, J=8.6 Hz), 7.16 (1H, t, J=6.6 Hz), 7.39 (2H, dd, J=8.6, 6.6 Hz), 7.57 (2H, d, J=8.6 Hz)

| Elementary analysis (for C$_{20}$H$_{21}$NO$_5$) | | | |
| --- | --- | --- | --- |
| | C | H | N |
| Calculated | 67.59 | 5.96 | 3.94 |
| Found | 67.67 | 5.96 | 3.93 |

Example 32

Using proper starting materials, compounds 190 and 191 shown in Table 14 were synthesized in the same manner as in Example 31.

Example 33

Using proper starting materials, compounds 192 and 193 shown in Table 14 were synthesized in the same manner as in Example 25.

Example 34

Synthesis of 3-{4-[3-(4-chlorophenyl)-2-oxooxazolidin-5-yl]methoxyphenyl}propyl alcohol Lithium aluminum hydride (59 mg) was added to a tetrahydrofuran (15 ml) solution of 750 mg of methyl 3-{4-[3-(4-chlorophenyl)-2-oxooxazolidin-5-yl]methoxyphenyl}propionate (compound 191) obtained in Example 32. The mixture was stirred with ice-cooling for 40 minutes in a stream of nitrogen. To the reaction mixture was added 5% hydrochloric acid, and the mixture was extracted with ethyl acetate. The extract was washed with an aqueous solution of sodium chloride, dried with magnesium sulfate and filtered. The filtrate was concentrated under reduced pressure. The residue was subjected to silica gel column chromatography and purified by hexane-ethyl acetate gradient elution to give 498 mg of the title compound (compound 194) in a yield of 71%.

Melting point: 119°–120° C. NMR spectrum (CDCl$_3$) δ1.27 (1H, br-s), 1.80–1.91 (2H, m), 2.66 (2H, t, J=7.6 Hz), 3.67 (2H, t, J=6.3 Hz), 4.04 (1H, dd, J=8.9, 5.9 Hz), 4.17 (1H, t, J=8.9 Hz), 4.20 (2H, d, J=4.6 Hz), 4.89–5.02 (1H, m), 6.83 (2H, d, J=8.6 Hz), 7.12 (2H, d, J=8.6 Hz), 7.34 (2H, d, J=8.9 Hz), 7.52 (2H, d, J=8.9 Hz)

| Elementary analysis (for C$_{19}$H$_{20}$NO$_4$Cl) | | | |
| --- | --- | --- | --- |
| | C | H | N |
| Calculated | 63.07 | 5.57 | 3.87 |
| Found | 62.77 | 5.56 | 3.87 |

Example 35

Synthesis of 3-[4-(3-phenyl-2-oxooxazolidin-5-yl)methoxyphenyl]propyl alcohol

The same procedure of Example 34 was repeated except that methyl 3-[4-(3-phenyl-2-oxooxazolidin-5-yl)methoxyphenyl]propionate (compound 189) obtained in Example 31 was used in lieu of methyl 3-{4-[3-(4-chlorophenyl)-2-oxooxazolidin-5-yl]methoxyphenyl}propionate to give the title compound (compound 195) in a yield of 48%.

Melting point: 123°–124° C. NMR spectrum (CDCl$_3$) δ1.27 (1H, br-s), 1.81–1.91 (2H, m), 2.66 (2H, t, J=7.6 Hz), 3.66 (2H, t, J=6.4 Hz), 4.06 (1H, dd, J=8.9, 5.9 Hz), 4.14–4.25 (3H, m), 4.93–5.02 (1H, m), 6.83 (2H, d, J=8.6 Hz), 7.12 (2H, d, J=8.6 Hz), 7.14 (1H, t, J=6.6 Hz), 7.39 (2H, dd, J=8.6, 6.6 Hz), 7.56 (2H, d, J=8.6 Hz)

| Elementary analysis (for C$_{19}$H$_{21}$NO$_4$) | | | |
| --- | --- | --- | --- |
| | C | H | N |
| Calculated | 69.71 | 6.47 | 4.28 |
| Found | 69.81 | 6.61 | 4.34 |

Example 36

Synthesis of methyl 3-{4-[3-(2-pyridyl)-2-oxooxazolidin-5-yl]methoxyphenyl}-2-bromopropionate A 0.90 g quantity of sodium nitrite was added to a solution of 3.30 g of 4-[3-(2-pyridyl)-2-oxooxazolidin-5-yl]methoxyaniline obtained in Reference Example 21 in 40 ml of methanol, 10 ml of acetone and 8.0 g of 47% hydrobromic acid. The mixture was stirred with ice-cooling for 0.5 hour. To the mixture was added 6.4 ml of methyl acrylate, and 256 mg of cuprous oxide was added thereto at 40° C. and the mixture was stirred at the same temperature for 20 minutes. The reaction mixture was concentrated under reduced pressure and the obtained residue was extracted with ethyl acetate. The extract was washed successively with aqueous ammonia and an aqueous solution of sodium chlorides, dried with magnesium sulfate and filtered. The filtrate was concentrated under reduced pressure. The residue was subjected to silica gel column chromatography and purified by hexane-ethyl acetate gradient elution to give 2.7 g of the title compound (compound 196) as an oil (yield 53%).

NMR spectrum (CDCl$_3$) δ3.18 (1H, dd, J=14.2, 7.9 Hz), 3.40 (1H, dd, J=14.2, 8.6 Hz), 3.72 (3H, s), 4.2–4.45 (4H, m), 5.02 (1H, m), 6.79 (2H, d, J=8.9 Hz), 7.05 (1H, dd, J=5.0, 4.0 Hz), 7.39 (2H, d, J=8.9 Hz), 7.73 (1H, ddd, J=8.6, 5.0, 1.0 Hz), 8.24 (1H, d, J=8.6 Hz), 8.34 (1H, dd, J=4.0, 1.0 Hz)

Example 37

Synthesis of methyl 3-[4-(3-phenyl-2-oxooxazolidin-5-yl)methoxyphenyl]-2-chloropropionate and methyl 3-{4-[3-(4-chlorophenyl)-2-oxooxazolidin-5-yl]methoxyphenyl}-2-chloropropionate The same procedure of Example 36 was repeated except that 2.89 g of a mixture of 4-[3-(4-chlorophenyl)-2-oxooxazolidin-5-yl]methoxyaniline and 4-(3-phenyl-2-oxooxazolidin-5-yl)methoxyaniline obtained in Reference Example 22 was used in lieu of 4-[3-(2-pyridyl)-2-oxooxazolidin-5-yl]methoxyaniline, and concentrated hydrochloric acid was used in lieu of 47% hydrobromic acid. The residue was subjected to silica gel chromatography and purified by hexane-ethyl acetate gradient elution to give 210 mg of methyl 3-[4-(3-phenyl-2-oxooxazolidin-5-yl)methoxyphenyl]-2-chloropropionate (compound 197) and 180 mg of methyl 3-{4-[3-(4-chlorophenyl)-2-oxooxazolidin-5-yl]methoxyphenyl}-2-chloropropionate (compound 198). Methyl 3-[4-(3-phenyl-2-oxooxazolidin-5-yl)methoxyphenyl]-2-chloropropionate Melting point 83°–84° C. NMR spectrum (CDCl₃) δ3.12 (1H, dd, J=14.2, 7.6 Hz), 3.31 (1H, dd, J=14.2, 7.1 Hz), 3.74 (3H, s), 4.06 (1H, dd, J=8.8, 6.1 Hz), 4.17–4–24 (3H, m), 4.40 (1H, dd, J=7.6, 7.3 Hz), 4.97 (1H, m), 6.85 (2H, d, J=8.6 Hz), 7.10–7.20 (3H, m), 7.40 (2H, dd, J=8.2, 7.6 Hz), 7.57 (2H, d, J=7.6 Hz)

|  | Elementary analysis (for C₂₀H₂₀NO₅Cl) | | |
|---|---|---|---|
|  | C | H | N |
| Calculated | 61.62 | 5.17 | 3.59 |
| Found | 61.71 | 5.07 | 3.63 |

Methyl 3-{4-[3-(4-chlorophenyl)-2-oxooxazolidin-5-yl]methoxyphenyl}-2-chloropropionate Melting point 94°–95° C. NMR spectrum (CDCl₃) δ3.10 (1H, dd, J=14.2, 7.2 Hz), 3.29 (1H, dd, J=14.2, 7.2 Hz), 3.73 (3H, s), 4.00 (1H, dd, J=8.9, 5.9 Hz), 4.11–4.23 (3H, m), 4.40 (1H, dd, J=7.6, 7.3 Hz), 4.95 (1H, m), 6.83 (2H, d, J=8.6 Hz), 7.13 (2H, d J=8.6 Hz), 7.32 (2H, d, J=8.9 Hz), 7.50 (2H, d, J=8.9 Hz)

|  | Elementary analysis (for C₂₀H₁₉NO₅Cl₂) | | |
|---|---|---|---|
|  | C | H | N |
| Calculated | 56.62 | 4.51 | 3.30 |
| Found | 56.70 | 4.44 | 3.30 |

The structures and properties of the compounds synthesized in Examples of the present invention are shown below.

TABLE 1

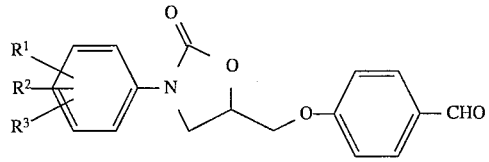

| Compound No. | R¹ | R² | R³ | Melting point (°C.) | Yield (%) | Elementary analysis (%) Calculated (Found) or H-NMR (DMSO-d₆) | | |
|---|---|---|---|---|---|---|---|---|
|  |  |  |  |  |  | C | H | N |
| 1 | 4-OMe | H | H | 135–137 | 91 | 66.05 (66.23 | 5.23 5.36 | 4.28 4.40) |
| 2 | 3-OMe | H | H | 177–179 | 86 | 66.05 (66.24 | 5.23 5.03 | 4.27 4.32) |
| 3 | 2-OMe | H | H | 93–95 | 42 | 66.05 (65.90 | 5.23 4.94 | 4.27 4.33) |
| 4 | 2-OMe | 4-OMe | H | 137–139 | 85 | 63.86 (63.48 | 5.36 5.48 | 3.92 3.81) |
| 5 | 4-OEt | H | H | 132–134 | 85 | 66.85 (66.94 | 5.61 5.75 | 4.10 4.12) |
| 6 | 2-OEt | H | H | Oil | 92 | 60.78 (60.66 | 4.88 4.89 | 6.16 6.04) |
| 7 | 4-Cl | H | H | 113–115 | 69 | 61.55 (61.52 | 4.25 4.25 | 4.22 4.26) |
| 8 | 2-F | 4-Br | H | 130–133 | 87 | 51.80 (51.78 | 3.32 3.34 | 3.55 3.61) |
| 9 | 4-F | H | H | 161–164 | 75 | 64.76 (64.72 | 4.48 4.44 | 4.44 4.41) |
| 10 | 2-F | 4-F | H | 129–131 | 79 | 61.26 (61.29 | 3.93 4.07 | 4.20 4.20) |
| 11 | 2-F | 4-F | 6-F | 115–116 | 53 | 58.13 (58.10 | 3.44 3.46 | 3.99 3.93) |
| 12 | 3-F | 4-F | H | 141–143 | 67 | 61.26 (61.31 | 3.93 3.97 | 4.20 4.15) |
| 13 | 2-Cl | 4-Cl | H | 111–113 | 37 | 55.76 (55.74 | 3.58 3.51 | 3.82 3.86) |
| 14 | 3-Cl | 4-Cl | H | 136–139 | 83 | 55.76 (55.81 | 3.58 3.69 | 3.82 3.84) |
| 15 | 3-F | H | H | 159–161 | 86 | 64.76 (64.90 | 4.48 4.48 | 4.44 4.41) |
| 16 | 2-Cl | H | H | 92–93 | 46 | 61.55 (61.58 | 4.25 4.17 | 4.22 4.22) |
| 17 | 2-F | 4-Cl | H | 129–131 | 70 | 58.38 (58.38 | 3.75 3.71 | 4.00 4.09) |
| 18 | 4-COOEt | H | H | 151–152 | 79 | 65.03 (65.12 | 5.18 5.22 | 3.79 3.81) |
| 19 | H | H | H | 168–169 | 81 | 68.68 (68.69 | 5.09 5.13 | 4.71 4.63) |
| 20 | 4-Me | H | H | 158–160 | 86 | 69.44 (69.66 | 5.50 5.73 | 4.50 4.59) |
| 21 | 4-Et | H | H | 120–122 | 78 | 70.14 (70.40 | 5.88 5.91 | 4.31 4.37) |
| 22 | 4-iso-Pr | H | H | 131–134 | 84 | 70.78 | 6.24 | 4.13 |

TABLE 1-continued

[Structure: R¹, R², R³ substituted phenyl-N(COO-)-CH2-CH(-)-CH2-O-C6H4-CHO]

| Compound No. | R¹ | R² | R³ | Melting point (°C.) | Yield (%) | Elementary analysis (%) Calculated (Found) or H-NMR (DMSO-d₆) | | |
|---|---|---|---|---|---|---|---|---|
| | | | | | | C | H | N |
| | | | | | | (70.73 | 6.20 | 4.11) |
| 23 | 3,4-cyclopentyl | | H | 140–142 | 94 | 71.20 (71.18 | 5.68 5.71 | 4.15 4.18) |
| 24 | 4-NMe₂ | H | H | 183–185 | 70 | 67.05 (67.18 | 5.92 6.00 | 8.23 8.24) |
| 25 | 4-O-iPr | H | H | 122–124 | 78 | 67.60 (67.75 | 5.95 6.01 | 3.94 4.01) |
| 26 | 4-OCF₃ | H | H | 96–98 | 33 | 56.70 (56.97 | 3.70 3.72 | 3.67 3.69) |
| 27 | 4-CF₃ | H | H | 129–130 | 85 | 59.18 (59.03 | 3.86 3.93 | 3.83 3.81) |
| 28 | 3-CF₃ | H | H | 119–120 | 58 | 59.18 (59.35 | 3.86 3.93 | 3.83 3.77) |
| 29 | 2-CF₃ | H | H | 64–66 (.⅓ H₂O) | 64 | 58.23 (58.23 | 3.98 3.86 | 3.77 3.79) |
| 30 | 3,4-OCH₂O | | H | 160–162 | 88 | 63.34 (63.39 | 4.43 4.50 | 4.10 4.11) |
| 31 | 3,4-OCH₂CH₂O | | H | 196–197 | 88 | 64.22 (64.32 | 4.82 4.87 | 3.94 3.96) |
| 32 | 4-oxazolyl | H | H | 230–232 | 49 | 65.93 (65.80 | 4.43 4.46 | 7.69 7.61) |
| 33 | 4-NO₂ | H | H | 167–169 | 99 | 59.65 (59.34 | 4.12 4.05 | 8.18 8.26) |
| 34 | 4-CN | H | H | 180–182 | 66 | 4.12(1H, dd), 4.30(1H, dd), 4.34(1H, dd), 4.42(1H, dd), 5.12(1H, m), 7.04(2H, d), 7.70(2H, d), 7.75(2H, d), 7.85(2H, d), 9.90(1H, s) | | |

TABLE 2

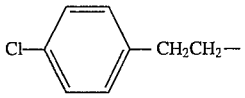

| Compound No. | R | —B— | Melting point (°C.) | Yield (%) | Elementary analysis (%) Calculated (Found) or H-NMR (DMSO-$d_6$) | | |
|---|---|---|---|---|---|---|---|
| | | | | | C | H | N |
| 35 | 4-Cl-C6H4-CH2CH2— | —CH2— | 67–69 | 82 | 62.38 (62.57 | 5.14 5.11 | 3.83 3.86) |
| 36 | MeO-C6H4— | —CH2CH2— | 116–117 | 57 | 66.85 (66.78 | 5.61 5.70 | 4.10 4.27) |
| 37 | CF3-C6H4— | —CH2CH2— | 129–131 | 53 | 60.16 (59.97 | 4.25 4.23 | 3.69 3.70) |
| 38 | 3-pyridyl | —CH2— | 135–137 | 27 | 4.00(1H, dd), 4.30(1H, dd), 4.40(1H, dd), 4.46(1H, dd), 5.16(1H, m), 7.17(2H, d), 7.45(1H, dd), 7.89(2H, d), 8.05(1H, ddd), 8.36(1H, dd), 8.80(1H, d), 9.89(1H, s) | | |
| 39 | 4-pyridyl | —CH2— | 153–155 | 58 | 3.96(1H, dd), 4.26(1H, dd), 4.40(1H, dd), 4.46(1H, dd), 5.16(1H, m), 7.16(2H, d), 7.58(1H, dd), 7.89(2H, d), 8.52(1H, dd), 9.89(1H, s) | | |

TABLE 3

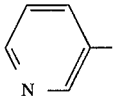

| Compound No. | R¹ | R² | R⁵ | Specific rotation $[\alpha]_D^{25}$ (concentration, solvent) | Melting point (°C.) | Yield (%) | Elementary analysis (%) Calculated (Found) | | |
|---|---|---|---|---|---|---|---|---|---|
| | | | | | | | C | H | N |
| 40 | 4-CF3 | H | H | −74.45° (1.0, CHCl3) | 132–133 | 68 | 59.18 (59.30 | 3.86 3.81 | 3.83 3.78) |
| 41 | 4-OMe | H | H | −78.68° (1.0, CHCl3) | 105–107 | 64 | 66.05 (65.76 | 5.23 5.53 | 4.28 4.49) |
| 42 | 4-Cl | 2-F | H | −88.62° (1.0, CHCl3) | 103–105 | 59 | 58.38 (58.43 | 3.75 3.58 | 4.00 4.05) |
| 43 | 4-F | 3-F | H | −69.19° (1.0, CHCl3) | 108–110 | 60 | 61.26 (61.22 | 3.93 3.89 | 4.20 4.18) |
| 44 | 4-OMe | H | Me | −75.79° (1.0, CHCl3) | Oil (⅓ H2O) | 85 | 66.16 (66.32 | 5.67 5.66 | 4.06 4.09) |

TABLE 4

![structure with R1, R2, R5, CHO]

| Compound No. | R¹ | R² | R⁵ | Specific rotation $[\alpha]_D^{25}$ (concentration, solvent) | Melting point (°C.) | Yield (%) | Elementary analysis (%) Calculated (Found) | | |
|---|---|---|---|---|---|---|---|---|---|
| | | | | | | | C | H | N |
| 45 | 4-CF₃ | H | H | +76.27° (1.0, CHCl₃) | 132–133 | 75 | 59.18 (59.23 | 3.89 3.82 | 3.83 3.80) |
| 46 | 4-OMe | H | H | +77.04° (1.0, CHCl₃) | 103–105 | 79 | 66.05 (65.99 | 5.23 5.38 | 4.28 4.65) |
| 47 | 4-Cl | 2-F | H | +87.59° (1.0, CHCl₃) | 105–107 | 64 | 58.38 (58.36 | 3.75 3.59 | 4.00 4.01) |
| 48 | 4-F | 3-F | H | +63.39° (1.0, CHCl₃) | 108–109 | 50 | 61.26 (61.32 | 3.93 3.92 | 4.20 4.19) |
| 49 | 4-OMe | H | Me | +72.39° (1.0, CHCl₃) | Oil (·⅓ H₂O) | 85 | 66.16 (66.34 | 5.67 5.77 | 4.06 4.04) |

TABLE 5

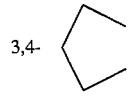

| Compound No. | R¹ | R² | R⁶ | Melting point (°C.) | Yield (%) | Elementary analysis (%) Calculated (Found) or H-NMR (DMSO-d₆) | | |
|---|---|---|---|---|---|---|---|---|
| | | | | | | C | H | N |
| 50 | 4-NO2 | H | Me | 200–201 | 90 | 58.07 (58.03 | 4.33 4.30 | 7.52 7.38) |
| 51 | 4-Cl | H | Me | 146–148 | 89 | 59.76 (59.88 | 4.46 4.39 | 3.87 3.88) |
| 52 | 4-Me | H | Me | 140–142 | 92 | 66.85 (66.85 | 5.61 5.54 | 4.10 4.06) |
| 53 | 4-Et | H | Me | 139–141 | 96 | 67.59 (67.50 | 5.96 5.83 | 3.94 3.93) |
| 54 | 4-iso-Pr | H | Me | 145–147 | 94 | 68.28 (68.26 | 6.28 6.30 | 3.79 3.95) |
| 55 | 4-t-Bu | H | Me | 175–177 | 95 | 68.91 (68.97 | 6.57 6.69 | 3.65 3.69) |
| 56 | 4-n-Bu | H | Me | 126–127 | 93 | 68.91 (68.88 | 6.57 6.62 | 3.65 3.65) |
| 57 | 4-iso-Bu | H | Me | 144–146 | 89 | 68.91 (68.91 | 6.57 6.60 | 3.65 3.63) |
| 58 | 3,4- (CH₂)₃ | | Me | 152–153 | 92 | 68.65 (68.67 | 5.76 5.71 | 3.81 3.79) |
| 59 | 3,4- OCH₂CH₂O | | Et | 137–138 | 72 | 63.15 (63.25 | 5.30 5.30 | 3.15 3.49) |
| 60 | 3-Cl | H | Me | 127–128 | 86 | 59.76 (59.86 | 4.46 4.42 | 3.87 3.86) |
| 61 | 4-Br | H | Me | 150–151 | 90 | 53.22 (53.19 | 3.97 3.85 | 3.45 3.40) |
| 62 | 2-F | H | Me | 116–118 | 83 | 62.61 (62.66 | 4.67 4.71 | 4.06 4.04) |
| 63 | 3-F | H | Me | 145–146 | 90 | 62.61 (62.81 | 4.67 4.64 | 4.06 4.13) |

TABLE 5-continued
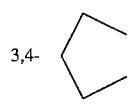
| Compound No. | R¹ | R² | R⁶ | Melting point (°C.) | Yield (%) | C | H | N |
|---|---|---|---|---|---|---|---|---|
| | | | | | | \multicolumn{3}{c}{Elementary analysis (%) Calculated (Found) or H-NMR (DMSO-d₆)} |
| 64 | 4-F | H | Me | 126–127 | 91 | 62.61 (62.74 | 4.67 4.59 | 4.06 4.06) |
| 65 | 3-Cl | 4-Cl | Me | 142–143 | 83 | 54.56 (54.60 | 3.82 3.72 | 3.54 3.59) |
| 66 | 2-Cl | 4-Cl | Me | 135–138 | 93 | 54.56 (54.41 | 3.82 3.76 | 3.54 3.53) |
| 67 | 2-F | 4-F | Me | 104–106 | 88 | 59.51 (59.51 | 4.16 4.16 | 3.86 3.87) |
| 68 | 2-F | 4-Br | Me | 154–155 | 79 | 50.96 (51.03 | 3.56 3.56 | 3.30 3.13) |
| 69 | 4-CF₃ | H | Me | 152–154 | 93 | 57.73 (57.73 | 4.08 3.99 | 3.54 3.60) |
| 70 | 3-OMe | H | Me | 124–126 | 95 | 63.86 (63.85 | 5.36 5.29 | 3.92 3.94) |
| 71 | 4-OMe | H | Me | 133–134 | 93 | 63.86 (63.83 | 5.36 5.37 | 3.92 3.97) |
| 72 | 4-OEt | H | Me | Oil | 83 | — | — | — |
| 73 | 4-O-iso-Pr | H | Me | 152–153 | 92 | 65.44 (65.40 | 6.01 6.20 | 3.63 3.85) |
| 74 | 2-OMe | 4-OMe | Me | 137–138 | 83 | 62.01 (62.06 | 5.46 5.47 | 3.62 3.61) |
| 75 | 4-OCF₃ | H | Me | 142–143 | 93 | 55.48 (55.47 | 3.92 3.87 | 3.41 3.41) |
| 76 | 4-Ac | H | Me | 168–169 | 94 | 65.03 (65.02 | 5.18 5.14 | 3.79 3.77) |
| 77 | 4-COOEt | H | Me | 139–140 | 97 | 63.15 (63.01 | 5.30 5.23 | 3.51 3.50) |
| 78 | 4-CN | H | Me | 155–156 | 91 | 64.77 (65.05 | 4.58 4.45 | 7.95 7.98) |
| 79 | H | H | Et | 93–94 | 53 | 66.85 (66.86 | 5.61 5.61 | 4.10 4.08) |
| 80 | 3-NO₂ | H | Me | 154–155 | 80 | 58.07 (57.94 | 4.33 4.13 | 7.52 7.73) |
| 81 | 4-NO₂ | H | H | 236–238 | 85 | 56.99 (57.13 | 3.94 4.16 | 7.82 7.82) |
| 82 | H | H | H | 248–249 | 93 | 65.17 (65.34 | 4.83 4.87 | 4.47 4.45) |
| 83 | 4-Me | H | H | 252–253 | 93 | 66.05 (66.16 | 5.23 5.24 | 4.28 4.26) |
| 84 | 4-Et | H | H | 233–234 | 93 | 66.85 (66.88 | 5.61 5.63 | 4.10 4.20) |
| 85 | 4-iso-Pr | H | H | 254–255 | 95 | 67.59 (67.81 | 5.96 5.91 | 3.94 4.00) |
| 86 | 4-t-Bu | H | H | 270–271 | 85 | 68.28 (68.10 | 6.28 6.27 | 3.79 3.73) |
| 87 | 4-n-Bu | H | H | 213–214 | 92 | 68.28 (68.28 | 6.28 6.24 | 3.79 3.81) |
| 88 | 4-iso-Bu | H | H | 220–221 | 83 | 68.28 (68.61 | 6.28 6.18 | 3.79 3.86) |
| 89 | 3,4- 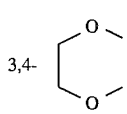 | | H | 257–260 | 96 | 67.98 (68.17 | 5.42 5.28 | 3.96 4.13) |
| 90 | 3,4- (dioxy) | | H | 239–240 | 83 | 61.45 (61.59 | 4.61 4.55 | 3.77 3.77) |
| 91 | 3-Cl | H | H | 220–222 | 87 | 58.72 (58.97 | 4.06 4.01 | 4.03 3.90) |
| 92 | 4-Cl | H | H | 240–242 | 89 | 58.72 (58.69 | 4.06 4.00 | 4.03 3.96) |

TABLE 5-continued

[Chemical structure: R¹ and R² substituted phenyl group attached via N to a 5-membered carbamate ring (oxazolidinone with C=O), connected through CH₂ to an O-linked para-substituted phenyl group with COOR⁶]

| Compound No. | R¹ | R² | R⁶ | Melting point (°C.) | Yield (%) | Elementary analysis (%) Calculated (Found) or H-NMR (DMSO-$d_6$) C | H | N |
|---|---|---|---|---|---|---|---|---|
| 93 | 4-Br | H | H | 260–261 | 97 | 52.06 (52.02 | 3.60 3.50 | 3.57 3.56) |
| 94 | 2-F | H | H | 164–166 | 81 | 61.63 (61.89 | 4.26 4.24 | 4.23 4.22) |
| 95 | 3-F | H | H | 229–230 | 85 | 61.63 (61.83 | 4.26 4.22 | 4.23 4.22) |
| 96 | 4-F | H | H | 229–231 | 82 | 61.63 (61.79 | 4.26 4.28 | 4.23 4.25) |
| 97 | 3-Cl | 4-Cl | H | 250–252 | 95 | 53.42 (53.31 | 3.43 3.41 | 3.66 3.70) |
| 98 | 2-Cl | 4-Cl | H | 218–220 | 61 | 53.42 (53.32 | 3.43 3.41 | 3.66 3.70) |
| 99 | 2-F | 4-F | H | 200–202 | 67 | 58.46 (58.54 | 3.75 3.76 | 4.01 4.01) |
| 100 | 2-F | 4-Br | H | 204–205 | 89 | 49.78 (49.63 | 3.19 3.18 | 3.41 3.35) |
| 101 | 4-CF₃ | H | H | 236–238 | 79 | 56.70 (56.82 | 3.70 3.73 | 3.67 3.74) |
| 102 | 4-OH | H | H | 271–272 | 76 | 62.00 (61.78 | 4.59 4.76 | 4.25 4.14) |
| 103 | 3-OMe | H | H | 209–211 | 87 | 61.12 (61.12 | 5.13 5.53 | 3.75 3.83) |
| 104 | 4-OMe | H | H | 211–213 | 84 | 62.97 (63.14 | 4.99 5.02 | 4.08 4.16) |
| 105 | 2-OMe | 4-OMe | H | 218–220 | 89 | 62.97 (63.13 | 4.99 4.86 | 4.08 4.02) |
| 106 | 4-OEt | H | H | 166–167 | 84 | 63.86 (63.62 | 5.36 5.29 | 3.92 3.93) |
| 107 | 4-O-iso-Pr | H | H | 231–232 | 89 | 64.68 (64.79 | 5.70 5.78 | 3.77 3.85) |
| 108 | 4-OCF₃ | H | H | 208–209 | 91 | 54.42 (54.33 | 3.55 3.53 | 3.53 3.51) |
| 109 | 4-Ac | H | H | 253–254 | 94 | 64.22 (64.23 | 4.82 4.81 | 3.94 3.95) |
| 110 | 4-COOH | H | H | >300 | 95 | 60.51 (60.10 | 4.23 4.12 | 3.92 3.85) |
| 111 | 3-NO₂ | H | H | 266–268 | 91 | 56.99 (56.61 | 3.94 3.83 | 7.82 8.11) |
| 112 | 4-NH₂ | H | Me | 139–142 | 100 | 3.81(1H, dd), 3.82(3H, s), 4.12(1H, dd), 4.30(1H, dd), 4.36(1H, dd), 5.01(1H, m), 6.58(2H, d), 7.09(2H, d), 7.18(2H, d), 7.93(2H, d) | | |
| 113 | 4-NHAc | H | Me | 188–190 | 99 | 61.77 (61.55 | 5.31 5.20 | 7.20 7.07) |
| 114 | 4-NH₂·HCl | H | H | 248–252 (decomp.) | 64 | 55.96 (55.65 | 4.70 4.64 | 7.68 7.69) |
| 115 | 4-NHAc | H | H | 288–291 | 88 | 61.62 (61.30 | 4.90 4.93 | 7.56 7.54) |
| 116 | 4-NMe₂ | H | Me | 170–172 | 86 | 64.85 (64.95 | 5.99 6.03 | 7.56 7.60) |

TABLE 6

[Structure: R¹, R², R³ substituted phenyl-N(C(=O)O-)CH-CH₂-O-C₆H₄-COOR⁶ oxazolidinone]

| Compound No. | R¹ | R² | R³ | R⁶ | Melting point (°C.) | Yield (%) | Elementary analysis (%) Calculated (Found) | | |
|---|---|---|---|---|---|---|---|---|---|
| | | | | | | | C | H | N |
| 117 | 2-F | 4-F | 6-F | Et | 67–69 | 71 | 57.73 (57.66 | 4.08 4.02 | 3.54 3.48) |
| 118 | 2-F | 4-F | 6-F | H | 223–224 | 55 | 55.59 (55.64 | 3.29 3.17 | 3.81 3.79) |

TABLE 7

[Structure: R¹-C₆H₄-A-N(C(=O)O-)CH-CH₂-O-C₆H₄-COOR⁶ oxazolidinone]

| Compound No. | R¹ | —A— | R⁶ | Melting point (°C.) | Yield (%) | Elementary analysis (%) Calculated (Found) | | |
|---|---|---|---|---|---|---|---|---|
| | | | | | | C | H | N |
| 119 | Me | —CO— | Me | 150–151 | 90 | 65.04 (65.40 | 5.18 5.20 | 3.79 3.78) |
| 120 | H | —CO— | CH₂C₆H₅ | 126–128 | 96 | 69.60 (69.78 | 4.91 4.90 | 3.25 3.21) |
| 121 | H | —CO— | Me | 138–139 | 86 | 68.91 (68.88 | 6.57 6.62 | 3.65 3.65) |
| 122 | H | —SO₂— | Me | 129–131 | 95 | 55.24 (55.34 | 4.38 4.29 | 3.58 3.55) |
| 123 | Me | —SO₂— | CH₂C₆H₅ | 146–147 | 93 | 62.36 (62.47 | 4.81 4.77 | 2.91 2.91) |
| 124 | H | —CH₂— | Me | 85–86 | 52 | 66.85 (66.85 | 5.61 5.63 | 4.10 4.08) |
| 125 | Me | —CH₂— | Me | 112–113 | 63 | 67.70 (67.66 | 5.96 5.98 | 3.94 4.03) |
| 126 | Cl | —CH₂— | Me | 67–70 | 61 | 60.72 (60.81 | 4.83 4.77 | 3.73 3.74) |
| 127 | H | —CH₂CH₂— | Me | 112–113 | 83 | 67.59 (67.72 | 5.96 5.95 | 3.94 3.94) |
| 128 | Me | —CH₂CH₂— | Me | 143–144 | 84 | 68.28 (68.35 | 6.28 6.24 | 3.79 3.77) |
| 129 | H | —CH₂— | H | 172–174 | 91 | 66.05 (66.09 | 5.23 5.53 | 4.28 4.33) |
| 130 | Me | —CH₂— | H | 188–189 | 62 | 66.85 (67.06 | 5.61 5.63 | 4.10 4.32) |
| 131 | Cl | —CH₂— | H | 197–199 | 75 | 59.76 (59.68 | 4.46 4.49 | 3.87 3.92) |
| 132 | H | —CH₂CH₂— | H | 194–196 | 73 | 66.85 (66.85 | 5.61 5.62 | 4.10 4.09) |
| 133 | Me | —CH₂CH₂— | H | 172–174 | 39 | 67.59 (67.69 | 5.96 6.00 | 3.94 4.07) |
| 134 | H | —CO— | H | 219–221 | 8 | 63.34 (63.24 | 4.43 4.37 | 4.10 4.07) |
| 135 | Me | —SO₂— | H | 252–254 | 62 | 55.24 (55.26 | 4.38 4.36 | 3.58 3.60) |

TABLE 8

[Structure: R¹, R² substituted phenyl-N-C(=O)-O-CH(CH₂-)-CH₂-O-C₆H₄-COOR⁶ (oxazolidinone)]

| Compound No. | R¹ | R² | R⁶ | Specific rotation [α]D²⁵ (concentration, solvent) | Melting point (°C.) | Yield (%) | Elementary analysis (%) Calculated (Found) C | H | N |
|---|---|---|---|---|---|---|---|---|---|
| 136 | H | H | Me | −75.5° (1.0, CH₂Cl₂) | 114–115 | 85 | 66.05 (65.90 | 5.23 5.12 | 4.28 4.26) |
| 137 | 4-t-Bu | H | Me | −75.8° (1.0, CH₂Cl₂) | 163–165 | 87 | 68.91 (68.99 | 6.57 6.68 | 3.65 3.74) |
| 138 | 4-CF₃ | H | Me | −67.5° (1.0, CH₂Cl₂) | 131–132 | 65 | 57.73 (57.68 | 4.08 3.93 | 3.54 3.61) |
| 139 | 4-OMe | H | Me | −69.9° (1.0, CH₂Cl₂) | 119–120 | 87 | 63.86 (63.76 | 5.36 5.32 | 3.92 3.93) |
| 140 | 4-Cl | H | Me | −84.8° (1.0, CH₂Cl₂) | 162–163 | 90 | 59.76 (59.68 | 4.46 4.37 | 3.87 3.85) |
| 141 | 3-Cl | 4-Cl | Me | −79.8° (1.0, CH₂Cl₂) | 167–168 | 88 | 54.56 (54.63 | 3.82 3.75 | 3.54 3.51) |
| 142 | 2-F | 4-Br | Me | −76.8° (1.0, CH₂Cl₂) | 136–137 | 80 | 50.96 (50.89 | 3.56 3.53 | 3.30 3.29) |
| 143 | 4-OCF₃ | H | Me | −63.1° (1.0, CH₂Cl₂) | 124–125 | 86 | 55.48 (55.66 | 3.92 3.79 | 3.41 3.42) |
| 144 | 4-Ac | H | Me | −107.6° (1.0, CH₂Cl₂) | 130–132 | 82 | 65.03 (65.00 | 5.18 5.24 | 3.79 3.79) |
| 145 | H | H | H | −99.3° (0.3, MeOH) | 218–219 | 92 | 65.17 (65.03 | 4.83 4.82 | 4.47 4.44) |
| 146 | 4-t-Bu | H | H | −96.0° (1.0, DMF) | 265–267 | 90 | 68.28 (68.02 | 6.28 6.25 | 3.79 3.78) |
| 147 | 4-CF₃ | H | H | −92.3° (0.5, MeOH) | 206–208 | 98 | 56.70 (56.86 | 3.70 3.64 | 3.67 3.70) |
| 148 | 4-OMe | H | H | −91.3° (0.3, MeOH) | 204–205 | 80 | 62.97 (62.75 | 4.99 4.89 | 4.08 4.01) |
| 149 | 4-Cl | H | H | −106.2° (0.5, MeOH) | 200–202 | 92 | 58.72 (58.50 | 4.06 4.03 | 4.03 3.93) |
| 150 | 3-Cl | 4-Cl | H | −115.0° (1.0, DMF) | 229–231 | 80 | 53.42 (53.29 | 3.43 3.38 | 3.66 3.58) |
| 151 | 2-F | 4-Br | H | −102.0° (0.5, MeOH) | 193–195 | 93 | 49.78 (49.69 | 3.19 3.12 | 3.41 3.35) |
| 152 | 4-OCF₃ | H | H | −81.4° (1.0, DMF) | 208–210 | 99 | 54.42 (54.59 | 3.55 3.50 | 3.53 3.58) |

TABLE 9

[Structure: enantiomer of Table 8 compound, with wedge/dash stereochemistry at the oxazolidinone ring]

| Compound No. | R¹ | R² | R⁶ | Specific rotation [α]D²⁵ (concentration, solvent) | Melting point (°C.) | Yield (%) | Elementary analysis (%) Calculated (Found) C | H | N |
|---|---|---|---|---|---|---|---|---|---|
| 153 | H | H | Me | +73.5° (1.0, CH₂Cl₂) | 110–113 | 75 | 66.05 (66.04 | 5.23 5.16 | 4.28 4.23) |
| 154 | 4-t-Bu | H | Me | +73.0° (1.0, CH₂Cl₂) | 163–164 | 83 | 68.91 (69.07 | 6.57 6.66 | 3.65 3.69) |
| 155 | 4-CF₃ | H | Me | +64.6° (1.0, CH₂Cl₂) | 125–127 | 37 | 57.73 (57.75 | 4.08 3.94 | 3.54 3.52) |
| 156 | 4-OMe | H | Me | +65.6° (1.0, CH₂Cl₂) | 127–129 | 84 | 63.86 (63.79 | 5.36 5.29 | 3.92 3.92) |
| 157 | 4-Cl | H | Me | +88.5° (1.0, CH₂Cl₂) | 162–163 | 93 | 59.76 (59.96 | 4.46 4.41 | 3.87 3.89) |
| 158 | 3-Cl | 4-Cl | Me | +86.0° (1.0, CH₂Cl₂) | 165–166 | 84 | 54.56 (54.67 | 3.82 3.77 | 3.54 3.49) |

TABLE 9-continued

[Structure: R¹, R² substituted phenyl-N-oxazolidinone-CH₂-O-phenyl-COOR⁶]

| Compound No. | R¹ | R² | R⁶ | Specific rotation [α]_D^25 (concentration, solvent) | Melting point (°C.) | Yield (%) | Elementary analysis (%) Calculated (Found) C | H | N |
|---|---|---|---|---|---|---|---|---|---|
| 159 | 2-F | 4-Br | Me | +82.8° (1.0, CH₂Cl₂) | 133–135 | 69 | 50.96 (50.84 | 3.56 3.49 | 3.30 3.21) |
| 160 | 4-OCF₃ | H | Me | +65.7° (1.0, CH₂Cl₂) | 123–124 | 84 | 55.48 (55.58 | 3.92 3.79 | 3.41 3.38) |
| 161 | H | H | H | +84.8° (0.3, MeOH) | 217–220 | 86 | 65.17 (65.11 | 4.83 4.72 | 4.47 4.49) |
| 162 | 4-t-Bu | H | H | +89.2° (1.0, DMF) | 265–267 | 90 | 68.28 (68.01 | 6.28 6.18 | 3.79 3.83) |
| 163 | 4-CF₃ | H | H | +83.4° (0.5, MeOH) | 194–197 | 73 | 56.70 (56.59 | 3.70 3.52 | 3.67 3.70) |
| 164 | 4-OMe | H | H | +87.2° (0.3, MeOH) | 193–195 | 88 | 62.97 (62.77 | 4.99 4.91 | 4.08 4.02) |
| 165 | 4-Cl | H | H | +114.4° (0.5, MeOH) | 199–201 | 86 | 58.72 (58.74 | 4.06 4.04 | 4.03 4.02) |
| 166 | 3-Cl | 4-Cl | H | +99.2° (1.0, DMF) | 225–227 | 85 | 53.42 (53.29 | 3.43 3.26 | 3.66 3.67) |
| 167 | 2-F | 4-Br | H | +93.6° (0.5, MeOH) | 186–188 | 91 | 49.78 (49.61 | 3.19 3.09 | 3.41 3.39) |
| 168 | 4-OCF₃ | H | H | +86.4° (1.0, DMF) | 209–211 | 98 | 54.42 (54.43 | 3.55 3.53 | 3.53 3.54) |

TABLE 10

[Structure: R¹ substituted phenyl-N-(thiono)oxazolidine-CH₂-O-phenyl-COOR⁶]

| Compound No. | R¹ | R⁶ | Melting point (°C.) | Yield (%) | Elementary analysis (%) Calculated (Found) C | H | N |
|---|---|---|---|---|---|---|---|
| 169 | H | Me | 144–145 | 50 | 62.96 (62.92 | 4.99 5.09 | 4.08 4.01) |
| 170 | Me | Me | 148–149 | 49 | 63.85 | 5.36 | 3.92 |
| | | | | | (63.95 | 5.26 | 3.93) |
| 171 | H | H | 214–215 | 33 | 61.99 (61.99 | 4.59 4.60 | 4.25 4.09) |

TABLE 11

[Structure: R¹ substituted phenyl-N-oxazolidinone with R⁴-CH₂-O-phenyl-Y]

| Compound No. | R¹ | R⁴ | —Y | Melting point (°C.) | Yield (%) | Elementary analysis (%) Calculated (Found) C | H | N |
|---|---|---|---|---|---|---|---|---|
| 172 | OMe | Me | —CHO | 115–116 | 80 | 66.85 (67.02 | 5.61 5.82 | 4.10 4.30) |

TABLE 12
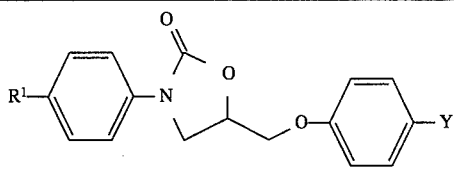
| Compound No. | R¹ | —Y | Melting point (°C.) | Yield (%) | Elementary analysis (%) Calculated (Found) | | |
|---|---|---|---|---|---|---|---|
| | | | | | C | H | N |
| 173 | CHO | —CHO | 130–132 | 89 | 66.46 (66.39 | 4.65 4.70 | 4.31 4.60) |
| 174 | Cl | —CH₂OH | 149–150 | 86 | 61.18 (61.40 | 4.83 4.74 | 4.20 4.27) |
| 175 | Me | —CH₂OH | 163–165 | 63 | 69.00 (69.04 | 6.11 6.24 | 4.47 4.40) |
TABLE 13
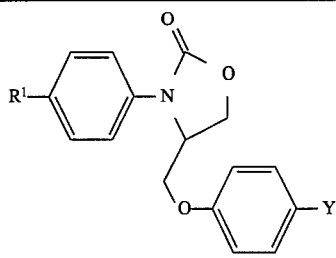
| Compound No. | R¹ | —Y | Melting point (°C.) | Yield (%) | Elementary analysis (%) Calculated (Found) | | |
|---|---|---|---|---|---|---|---|
| | | | | | C | H | N |
| 176 | Cl | —COOMe | 135–136 | 90 | 59.76 (59.67 | 4.46 4.56 | 3.87 3.96) |
| 177 | H | —COOMe | 158–159 | 60 | 66.05 (66.09 | 5.23 5.21 | 4.28 4.34) |
| 178 | Cl | —CHO | 120–122 | 92 | 61.55 (61.48 | 4.25 4.70 | 4.22 4.22) |
| 179 | Cl | —COOH | 219–221 | 64 | 66.05 (66.09 | 5.23 5.21 | 4.28 4.34) |
| 180 | H | —COOH | 255–257 | 61 | 64.43 (64.57 | 4.90 4.81 | 4.42 4.39) |
TABLE 14
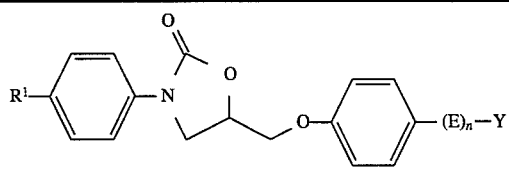
| Compound No. | R¹ | —(E)ₙ—Y | Melting point (°C.) | Yield (%) | Elementary analysis (%) Calculated (Found) | | |
|---|---|---|---|---|---|---|---|
| | | | | | C | H | N |
| 181 | H | ⟋⟍COOH | 239–240 | 84 | 67.25 (67.59 | 5.05 4.95 | 4.13 4.28) |

TABLE 14-continued

Structure: R¹—(phenyl)—N(C(=O)O—)—CH2—CH(—O—)—CH2—O—(phenyl)—(E)ₙ—Y (oxazolidinone ring)

| Compound No. | R¹ | —(E)ₙ—Y | Melting point (°C.) | Yield (%) | C | H | N |
|---|---|---|---|---|---|---|---|
| 182 | CF₃ | CH=CH-COOH | 234–236 | 97 | 58.97 (58.63 | 3.96 4.03 | 3.44 3.68) |
| 183 | Cl | CH=CH-COOH | 223–224 | 84 | 61.05 (61.33 | 4.31 4.41 | 3.75 4.17) |
| 184 | Me | CH=CH-COOH | 241–243 | 93 | 67.98 (68.06 | 5.42 5.40 | 3.96 4.02) |
| 185 | H | CH=CH-COOMe | 179–181 | 94 | 67.98 (67.51 | 5.42 5.66 | 3.96 3.97) |
| 186 | CF₃ | CH=CH-COOMe | 187–188 | 92 | 59.86 (59.93 | 4.31 4.28 | 3.32 3.40) |
| 187 | Cl | CH=CH-COOMe | 170–172 | 84 | 61.94 (61.91 | 4.68 4.84 | 3.61 3.69) |
| 188 | Me | CH=CH-COOMe | 183–185 | 97 | 68.65 (68.84 | 5.76 5.86 | 3.81 3.75) |
| 189 | H | CH2CH2-COOMe | 138–139 | 88 | 67.59 (67.67 | 5.96 5.96 | 3.94 3.93) |
| 190 | CF₃ | CH2CH2-COOMe | 136–137 | 88 | 59.57 (59.68 | 4.76 4.69 | 3.31 3.29) |
| 191 | Cl | CH2CH2-COOMe | 133–134 | 85 | 61.62 (61.75 | 5.17 5.17 | 3.59 3.57) |
| 192 | H | CH2CH2-COOH | 185–187 | 79 | 66.85 (66.83 | 5.61 5.68 | 4.10 4.08) |
| 193 | Cl | CH2CH2-COOH | 162–163 | 79 | 60.71 (60.70 | 4.83 4.78 | 3.73 3.77) |
| 194 | Cl | CH2CH2-CH2OH | 119–120 | 71 | 63.07 (62.77 | 5.57 5.56 | 3.87 3.87) |
| 195 | H | CH2CH2-CH2OH | 123–124 | 48 | 69.71 (69.81 | 6.47 6.61 | 4.28 4.34) |

TABLE 15

Structure: R¹—(pyridyl with X)—N(C(=O)O—)—CH2—CH(—O—)—CH2—O—(phenyl)—(E)ₙ—Y

| Compound No. | R¹ | X | —(E)ₙ—Y | Melting point (°C.) | Yield (%) | C | H | N |
|---|---|---|---|---|---|---|---|---|
| 196 | H | N | CH2CH(Br)-COOMe | Oil | 53 | 3.18(1H, dd), 3.40(1H, dd), 3.72(3H, s), 4.2–4.45 (4H, m), 5.02(1H, m), 6.79(2H, d), 7.05(1H, dd), 7.39(2H, d), 7.73(1H, ddd), 8.24(1H, d), 8.34(1H, dd) | | |

TABLE 15-continued

Structure: R¹-substituted phenyl-X ring with N-C(=O)-O-CH₂-CH(-CH₂-O-phenyl-(E)ₙ-Y)

| Compound No. | R¹ | X | —(E)ₙ—Y | Melting point (°C.) | Yield (%) | Elementary analysis (%) Calculated (Found) or H-NMR (DMSO-d₆) | | |
|---|---|---|---|---|---|---|---|---|
| | | | | | | C | H | N |
| 197 | H | C | CH₂-CH(Cl)-COOMe | 83–84 | — | 61.62 (61.71 | 5.17 5.07 | 3.59 3.63) |
| 198 | 4-Cl | C | CH₂-CH(Cl)-COOMe | 94–95 | — | 56.62 (56.70 | 4.51 4.44 | 3.30 3.30) |

Preparation Examples

Given below are preparation examples wherein the compounds of the present invention are used. Preparation Example 1 Tablets Tablets were prepared in a conventional manner using the following components in the proportions indicated below.

| | |
|---|---|
| Compound 8 | 100 mg |
| Lactose | 47 mg |
| Corn starch | 50 mg |
| Crystalline cellulose | 50 mg |
| Hydroxypropyl cellulose | 15 mg |
| Talc | 2 mg |
| Magnesium stearate | 2 mg |
| Ethyl cellulose | 30 mg |
| Unsaturated fatty acid glyceride | 2 mg |
| Titanium dioxide | 2 mg |
| Per tablet | 300 mg |

Preparation Example 2 Granules

Granules were prepared in a conventional manner using the following components in the proportions indicated below.

| | |
|---|---|
| Compound 81 | 200 mg |
| Mannitol | 540 mg |
| Corn starch | 100 mg |
| Crystalline cellulose | 100 mg |
| Hydroxypropyl cellulose | 50 mg |
| Talc | 10 mg |
| Per wrapper | 1000 mg |

Preparation Example 3 Fine granules

Fine granules were prepared in a conventional manner using the following components in the proportions indicated below.

| | |
|---|---|
| Compound 83 | 200 mg |
| Mannitol | 520 mg |
| Corn starch | 100 mg |
| Crystalline cellulose | 100 mg |
| Hydroxypropyl cellulose | 70 mg |
| Talc | 10 mg |
| Per wrapper | 1000 mg |

Preparation Example 4 Capsules

Capsules are prepared in a conventional manner using the following components in the proportions indicated below.

| | |
|---|---|
| Compound 93 | 100 mg |
| Lactose | 50 mg |
| Corn starch | 47 mg |
| Crystalline cellulose | 50 mg |
| Talc | 2 mg |
| Magnesium stearate | 1 mg |
| Per capsule | 300 mg |

Preparation Example 5 Syrups

Syrup was prepared in a conventional manner using the following components in the quantities indicated below.

| | |
|---|---|
| Compound 98 | 1 g |
| Purified sucrose | 60 g |
| Ethyl parahydroxybenzoate | 5 mg |
| Butyl parahydroxybenzoate | 5 mg |
| Flavor | suitable amount |
| Coloring agent | suitable amount |
| Purified water | q.s. |
| Total | 100 ml |

Preparation Example 6 Injections

Injection was prepared in a conventional manner using the following components in the quantities indicated below.

| Compound 130 | 100 mg |
|---|---|
| Distilled water for injection | q.s. |
| Per ampule | 2 ml |

Preparation Example 7 Suppositories

Suppositories were prepared in a conventional manner using the following components in the proportions indicated below.

| Compound 147 | 100 mg |
|---|---|
| Witepsol W-35 (Trademark of Dynamite Nobel, a mixture of mono-, di- and tri-glycerides of saturated fatty acid from lauric acid to stearic acid) | 1400 mg |
| Per suppository | 1500 mg |

Pharmacological Test Example 1

Effects on sterol and fatty acid biosynthesis systems obtained from a rat liver slices Pharmacological tests were carried out according to the procedure mentioned below, referring to the following document: Endo, A., Tsujita, Y., Kuroda, M. and Tanzawa, K., Eur. J. Biochem., 77, 31–36 (1977).

The liver was extirpated from a male Wistar rat (body weight: about 200 g) immediately after sacrifice by decapitation, and sufficiently perfused with ice-cold Krebs-Ringer bicarbonate buffer solution. The liver slices (100 mg) were added to 1 ml of Krebs-Ringer bicarbonate buffer solution containing [$1$-$^{14}$C] acetic acid (2 µci/µmol) and one of test compounds adjusted to various concentrations, and the reaction was carried out at 37° C. for 2 hours in 95% $O_2$-5% $CO_2$ gas mixture. After cooling the reaction mixture, 2 ml of petroleum ether was added thereto to extract the sterol fraction with shaking. The extract was concentrated and 1 ml of 1% digitonin solution was added thereto. After standing, the mixture was centrifuged. The sterol fraction obtained as the sediment was washed several times with an organic solvent and dissolved in 1 ml of acetic acid. Subsequently, radioactivity of the sterol fraction was measured. Then the concentration of the test compound ($IC_{50}$) was determined at which the radioactivity was inhibited by 50% compared with the radioactivity observed in the control group wherein the test compounds were not used.

In a similar manner, the radioactivity of fatty acid fraction was determined which was obtained by treating, with hydrochloric acid, the lower layer of the petroleum ether mentioned in the above procedure.

The results are shown in Table 16.

TABLE 16

| Compound | $IC_{50}$ (µM) | |
|---|---|---|
| No. | Sterol | Fatty acid |
| 1 | 10.2 | 5.6 |

TABLE 16-continued

| Compound | $IC_{50}$ (µM) | |
|---|---|---|
| No. | Sterol | Fatty acid |
| 8 | 6.4 | 2.9 |
| 81 | 3.79 | 1.30 |
| 83 | 5.74 | 2.89 |
| 93 | 3.23 | 1.55 |
| 101 | 4.80 | 3.17 |
| 130 | 29.52 | 14.80 |
| 147 | 8.08 | 4.78 |
| 149 | 3.36 | 1.99 |
| 164 | 0.84 | 1.23 |
| 165 | 1.15 | 1.09 |
| 171 | 34.50 | 9.81 |
| 175 | 4.8 | 2.7 |
| 180 | 7.1 | 33.7 |
| 183 | 17.4 | 5.7 |
| 193 | 16.4 | 3.8 |
| 194 | 4.8 | 4.0 |
| 195 | 23.2 | 7.3 |

Pharmacological Test Example 2

Male Sprague-Dawley rats (body weight: about 130 g) were preliminarily bred for one week, and divided into groups, each group consisting of five rats. Each of the test compounds was suspended in a 0.5% hydroxy-propylmethylcellulose (HPMC) aqueous solution, and the suspensions were orally administered to the rats at a dose of 300 mg/kg at 9:00 a.m. everyday for 14 days. Twenty-four hours after the last administration, the rats were subjected to celiotomy under etherization and blood was drawn from the inferior vena cava. The blood was allowed to stand and centrifuged to obtain serum. Lipid (triglyceride and cholesterol) in the obtained serum was measured by the enzymic method using an autoanalyzer.

Pharmacological activities of the test compounds were determined as the rate of decrease (%) in serum lipid compared with the control group to which only 0.5% aqueous HPMC solution was administered.

The results are shown in Table 17.

TABLE 17

| Compound No. | Rate of decrease in total cholesterol in serum (%) | Rate of decrease in triglyceride in serum (%) |
|---|---|---|
| 98 | 26.8 | 65.5 |
| 100 | 32.4 | 62.9 |
| 108 | 50.4 | 83.0 |

We claim:

1. An oxazolidine derivative represented by the formula (I)

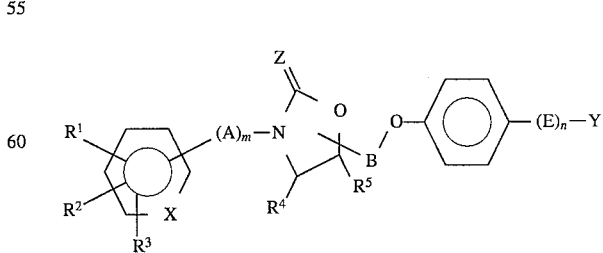

wherein $R^1$, $R^2$ and $R^3$ are the same or different, and each represents a hydrogen atom, a lower straight- or branched-chain alkyl group optionally having one or more halogen atoms, a lower alkoxy group optionally having one or more halogen atoms, a hydroxyl group, a halogen atom, a nitro group, an amino group optionally having one or more acetyl or lower alkyl groups, a carboxyl group, a lower alkoxycarbonyl group, a cyano group, a lower alkanoyl group or a 2-oxazolyl group, or $R^1$ and $R^2$ may be combined with each other to represent an alkylene chain —$(CH_2)_p$— or an alkylenedioxy chain —$O(CH_2)_qO$— wherein p is 3, 4 or 5, q is 1, 2 or 3, thus forming a cyclic structure, m and n are each 0 or 1, $R^4$ and $R^5$ are the same or different and each represents a hydrogen atom or a lower alkyl group, X is a carbon atom, Y is a carboxy group, A is a lower alkylene group, a carbonyl group or a sulfonyl group, B is a lower alkylene group, E is a lower alkylene group which may be halogen-substituted or is a lower alkenylene group, Z is an oxygen atom or a sulfur atom, with the proviso that a compound wherein at least two of $R^1$, $R^2$ and $R^3$ represent a nitro group is excluded, and that a compound, wherein at least two of $R^1$, $R^2$ and $R^3$ represent a branched-chain alkyl group and the substitution positions of these branched-chain alkyl groups are adjacent to each other, is excluded; or a pharmaceutically acceptable salt thereof.

2. An oxazolidine derivative according to claim 1 wherein m is 0 or a pharmaceutically acceptable salt thereof.

3. An oxazolidine derivative according to claim 1 wherein n is 0 or a pharmaceutically acceptable salt thereof.

4. An oxazolidine derivative according to claim 1 wherein B is bonded to the 5-position of the oxazolidine ring or a pharmaceutically acceptable salt thereof.

5. An oxazolidine derivative according to claim 1 wherein $R^4$ is a hydrogen atom or a pharmaceutically acceptable salt thereof.

6. An oxazolidine derivative according to claim 1 wherein $R^5$ is a hydrogen atom or a pharmaceutically acceptable salt thereof.

7. An oxazolidine derivative according to claim 1 wherein Z is an oxygen atom or a pharmaceutically acceptable salt thereof.

8. An oxazolidine derivative according to claim 1 wherein m is 0, B is bonded to the 5-position of the oxazolidine ring, $R^4$ and $R^5$ represent a hydrogen atom, and Z is an oxygen atom or a pharmaceutically acceptable salt thereof.

9. An oxazolidine derivative according to claim 1 wherein m and n are each 0, B is bonded to the 5-position of the oxazolidine ring, $R^4$ and $R^5$ represent a hydrogen atom, and Z is an oxygen atom or a pharmaceutically acceptable salt thereof.

10. An anti-hyperlipidemic composition containing an effective amount of the oxazolidine derivative of claim 1 or a pharmaceutically acceptable salt thereof and a pharmaceutically acceptable carrier.

11. A method for treating hyperlipidemia comprising administering to a patient in need of such treatment an effective amount of oxazolidine derivative represented by the formula (I)

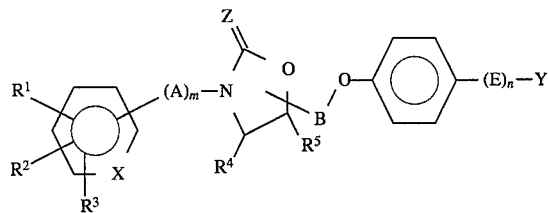

wherein $R^1$, $R^2$ and $R^3$ are the same or different, and each represents a hydrogen atom, a lower straight- or branched-chain alkyl group optionally having one or more halogen atoms, a lower alkoxy group optionally having one or more halogen atoms, a hydroxyl group, a halogen atom, a nitro group, an amino group optionally having one or more acetyl or lower alkyl groups, a carboxyl group, a lower alkoxycarbonyl group, a cyano group, a lower alkanoyl group or a 2-oxazolyl group, or $R^1$ and $R^2$ may be combined with each other to represent an alkylene chain —$(CH_2)_p$— or an alkylenedioxy chain —$O(CH_2)_qO$— wherein p is 3, 4 or 5, q is 1, 2 or 3, thus forming a cyclic structure, m and n are each 0 or 1, $R^4$ and $R^5$ are the same or different and each represents a hydrogen atom or a lower alkyl group, X is a carbon atom, Y is a hydroxymethyl group, an aldehyde group or a group represented by $COOR^6$ ($R^6$ is a lower alkyl group, a benzyl group or a hydrogen atom), A is a lower alkylene group, a carbonyl group or a sulfonyl group, B is a lower alkylene group, E is a lower alkylene group which may be halogen-substituted or is a lower alkenylene group, Z is an oxygen atom or a sulfur atom, with the proviso that when n is O, a compound wherein m is 1 and Y is a hydroxymethyl group is excluded; that when n is O, a compound wherein Y is a group represented by $COOR^6$ ($R^6$ is a lower alkyl group) is excluded; that a compound wherein at least two of $R^1$, $R^2$ and $R^3$ represent a nitro group is excluded; and that a compound, wherein at least two of $R^1$, $R^2$, and $R^3$ represent a branched-chain alkyl group and the substitution positions of these branched-chain alkyl groups are adjacent to each other is excluded; or a pharmaceutically acceptable salt thereof.

* * * * *

UNITED STATES PATENT AND TRADEMARK OFFICE
CERTIFICATE OF CORRECTION

PATENT NO. : 5,480,899

DATED : January 2, 1996

INVENTOR(S) : Shingo Yano, et al.

It is certified that error appears in the above-identified patent and that said Letters Patent is hereby corrected as shown below:

Column 68, line 65, at the end of the formula, insert --(I)--.

Column 70, line 15, at the end of the formula, insert --(I)--.

Column 70, line 40, change "O" to --0--.

Column 70, line 41, change "O" to --0--.

Signed and Sealed this

Twenty-second Day of June, 1999

Attest:

Q. TODD DICKINSON

*Attesting Officer*      *Acting Commissioner of Patents and Trademarks*